US007816314B2

(12) United States Patent
Scheper et al.

(10) Patent No.: US 7,816,314 B2
(45) Date of Patent: Oct. 19, 2010

(54) AUTOMATIC DISHWASHING COMPOSITIONS AND METHODS FOR USE WITH ELECTROCHEMICAL CELLS AND/OR ELECTROLYTIC DEVICES

(75) Inventors: William Michael Scheper, Lawrenceburg, IN (US); Kenneth Nathan Price, Cincinnati, OH (US); Mario Elmen Tremblay, West Chester, OH (US); Paul Joseph Drzewiecki, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1058 days.

(21) Appl. No.: 11/444,666

(22) Filed: Jun. 1, 2006

(65) Prior Publication Data
US 2006/0217280 A1  Sep. 28, 2006

Related U.S. Application Data

(63) Continuation of application No. 10/954,696, filed on Sep. 30, 2004, now abandoned, which is a continuation of application No. 10/222,644, filed on Aug. 16, 2002, now Pat. No. 6,921,743.

(60) Provisional application No. 60/381,472, filed on May 17, 2002, provisional application No. 60/381,455, filed on May 17, 2002, provisional application No. 60/381,146, filed on May 17, 2002, provisional application No. 60/381,473, filed on May 17, 2002.

(51) Int. Cl.
C11D 3/395 (2006.01)
C11D 7/10 (2006.01)

(52) U.S. Cl. .................. 510/224; 510/220; 510/226; 510/298; 510/379; 510/382; 510/445; 510/446; 510/480; 510/514

(58) Field of Classification Search .................. 510/220, 510/224, 226, 298, 379, 382, 445, 446, 480, 510/514
See application file for complete search history.

(56) References Cited

U.S. PATENT DOCUMENTS

| 3,616,355 A | 10/1971 | Themy et al. |
| 3,682,190 A * | 8/1972 | Patil et al. .................. 137/93 |
| 4,048,047 A | 9/1977 | Beck et al. |
| 4,062,754 A | 12/1977 | Eibl |
| 4,100,052 A | 7/1978 | Stillman |
| 4,328,084 A | 5/1982 | Shindell |
| 4,332,691 A | 6/1982 | Beavan |
| 4,402,197 A * | 9/1983 | Groult et al. .................. 68/12.21 |
| 4,434,629 A | 3/1984 | Bianchi et al. |
| 4,481,086 A * | 11/1984 | Bianchi et al. .................. 204/229.6 |
| 4,493,760 A | 1/1985 | Bianchi |
| 4,761,208 A | 8/1988 | Gram et al. |
| 5,080,819 A * | 1/1992 | Morganson et al. .................. 510/225 |
| 5,133,892 A * | 7/1992 | Chun et al. .................. 510/224 |
| 5,250,160 A * | 10/1993 | Oksman et al. .................. 205/701 |
| 5,314,589 A | 5/1994 | Hawley |
| 5,395,492 A | 3/1995 | Schoeberl |
| 5,439,576 A | 8/1995 | Schoeberl |
| 5,510,052 A | 4/1996 | McCandlish |
| 5,534,120 A | 7/1996 | Ando et al. |
| 5,837,663 A * | 11/1998 | Nicholson et al. .................. 510/226 |
| 5,865,966 A | 2/1999 | Watanabe et al. |
| 5,932,171 A | 8/1999 | Malchesky |
| 5,947,135 A | 9/1999 | Sumida et al. |
| 5,954,939 A | 9/1999 | Kanekuni et al. |
| 6,387,862 B2 * | 5/2002 | Busch et al. .................. 510/311 |
| 6,730,646 B1 * | 5/2004 | Waschenbach et al. .................. 510/224 |
| 7,015,184 B2 | 3/2006 | Yoneda et al. |
| 2002/0023847 A1 * | 2/2002 | Natsume .................. 205/687 |
| 2003/0109398 A1 * | 6/2003 | Yoneda et al. .................. 510/276 |
| 2004/0058846 A1 * | 3/2004 | Kistenmacher et al. .................. 510/475 |
| 2004/0102353 A1 * | 5/2004 | Lentsch et al. .................. 510/445 |
| 2004/0149571 A1 * | 8/2004 | Tremblay et al. .................. 204/275.1 |

FOREIGN PATENT DOCUMENTS

| EP | 0 038 100 A1 | 10/1981 |
| EP | 0 983 806 A1 | 3/2000 |
| GB | 2120282 | * 11/1983 |
| JP | 08-323307 | 12/1996 |
| JP | 1997122060 A | 5/1997 |
| JP | 09-201323 | 8/1997 |
| JP | 1998033448 A | 2/1998 |
| JP | 1998057297 A | 3/1998 |
| JP | 1998178491 A | 6/1998 |
| JP | 1998179489 A | 7/1998 |
| JP | 2000116587 A | 4/2000 |

(Continued)

OTHER PUBLICATIONS

U.S. Appl. No. 11/300,985, filed Dec. 15, 2005, Price et al.

Primary Examiner—Charles I Boyer
(74) Attorney, Agent, or Firm—Julie A. McConihay; Leonard W. Lewis; Steven W. Miller

(57) ABSTRACT

The present invention relates to automatic dishwashing detergent compositions and methods of using compositions comprising halogenated salts, phosphate and/or silicate in conjunction with electrolyzed water in automatic dishwashing appliances comprising an electrochemical cell and/or electrolytic device for treating tableware to improve cleaning, sanitizing and stain removal by controlling hardness, corrosion and dispersancy.

11 Claims, No Drawings

FOREIGN PATENT DOCUMENTS

| | | |
|---|---|---|
| JP | 2001 271098 A | 10/2001 |
| WO | WO 93/21298 | 10/1993 |
| WO | WO 93/21299 | 10/1993 |
| WO | WO 97/34987 | 9/1997 |
| WO | WO 99/34723 | 7/1999 |
| WO | WO 00/34184 | 6/2000 |
| WO | WO 00/64325 | 11/2000 |
| WO | WO 01/29166 A1 | 4/2001 |

\* cited by examiner

AUTOMATIC DISHWASHING COMPOSITIONS AND METHODS FOR USE WITH ELECTROCHEMICAL CELLS AND/OR ELECTROLYTIC DEVICES

CROSS REFERENCE TO RELATED PATENT APPLICATIONS

This application is a continuation application of U.S. patent application Ser. No. 10/954,696, filed Sep. 30, 2004 which is a continuation of U.S. application Ser. No. 10/222,644 filed Aug. 16, 2002 which claims benefit of the filing which claims priority to U.S. Provisional Application No. 60/381,472 filed May 17, 2002; U.S. Provisional Application No. 60/381,455 filed May 17, 2002; U.S. Provisional Application No. 60,381,146 filed May 17, 2002 and U.S. Provisional Application No. 60/381,473 filed May 17, 2002.

FIELD OF THE INVENTION

The present invention relates to automatic dishwashing detergent (ADD) compositions and methods of using compositions comprising halogenated salts, phosphate, and/or silicate in conjunction with electrolyzed water in automatic dishwashing appliances comprising an electrochemical cell and/or electrolytic device for treating tableware to improve cleaning, sanitizing and stain removal by controlling hardness, corrosion and dispersancy.

BACKGROUND OF THE INVENTION

Electrochemical cells for use in automatic dishwashing appliances are designed to operate by making use of the water electrolysis process wherein, at the anode-water interface, OH– being present in water due to electrolytic dissociation of water molecules donates an electron to the anode and can be thereby oxidized to oxygen gas which can be removed from the system. As a result, the H+ concentration can be enhanced at the anode-water interface so that H+ enriched acidic water can be produced. In a similar manner, at the cathode-water interface, H+ accepts an electron from the cathode and can be reduced to hydrogen to form hydrogen gas which can be similarly eliminated from the system so that the OH– concentration can be increased at the cathode-water interface whereby OH– enriched alkaline water can be generated. Further, when a halogen-containing water (such as, natural water containing sodium chloride or an aqueous solution of sodium chloride) can be subjected to electrolysis, halogenated mixed oxidants are generated in the electrolyzed water.

The following references disclose use of electrochemical cells: U.S. Pat. No. 5,932,171; U.S. Pat. No. 4,481,086; U.S. Pat. No. 4,434,629; U.S. Pat. No. 4,493,760; U.S. Pat. No. 4,402,197; U.S. Pat. No. 5,250,160; U.S. Pat. No. 5,534,120; U.S. Pat. No. 5,865,966; U.S. Pat. No. 5,947,135; JP Application No. 10057297A; JP Application No. 10179489A; JP Application No. 10033448A; JP Patent No. 09122060; JP Patent No. 2000116587; JP Patent No. 10178491; and EP Application No. 0983806A1.

The following references are also related to electrolyzed water: U.S. Pat. No. 3,616,355; U.S. Pat. No. 4,048,047; U.S. Pat. No. 4,062,754; U.S. Pat. No. 4,100,052; U.S. Pat. No. 4,328,084; U.S. Pat. No. 4,761,208; U.S. Pat. No. 5,314,589; U.S. Pat. No. 5,395,492; U.S. Pat. No. 5,439,576; U.S. Pat. No. 5,954,939 (equiv. EP 711,730); and WO 00/34184.

A problem associated with using an automatic dishwashing appliance containing an electrochemical cell and/or electrolytic device (hereinafter "cell and/or device") to produce electrolyzed water for cleaning tableware in the absence of a specific ADD composition can be that there can be a potential for serious consumer dissatisfaction with the performance results. While use of electrolyzed waster alone provides a source of alkalinity and bleaching agent, it nonetheless lacks the ability to control hardness, dispersancy and/or corrosion, and therefore can result in unsatisfactory performance. Though some of the references disclose the use of detergent ingredients in conjunction with electrolyzed water, they are either not related to treating tableware in automatic dishwashing applications and/or do not provide for the control of hardness, dispersancy and/or corrosion required by the present invention.

U.S. Pat. No. 5,932,171 discloses a phosphate can be used in conjunction with electrolyzed water for sterilizing medical instruments in an immersive-type sterilization bath, but does not disclose or suggest the use of phosphate in an ADD composition in conjunction with electrolyzed water to control hardness, dispersancy and/or corrosion. Furthermore, this reference broadly discloses the use of electrolyzed water in conjunction with an "anticorrosive," but fails to disclose specific anticorrosives (such as silicates, which are some of the most well known anticorrosives) or other "buffer additives."

Similarly, U.S. Pat. No. 5,250,160 discloses a phosphate can be used in conjunction with electrolyzed water for sterilizing objects in an immersive-type sterilization bath, but does not disclose or suggest the use of phosphate in an ADD composition for building and/or cleaning purposes, or to control hardness, dispersancy and/or corrosion. Although this reference generally describes the use of electrolyzed water in conjunction with simple phosphates, the function of the phosphate disclosed by the reference can be simply to provide electrolytes to aid in the process of electrolysis.

JP Application No. 10179489A describes the use of detergent in conjunction with electrolyzed water but specifically teaches that the best mode reduces or abolishes the need for a detergent. U.S. Pat. No. 4,402,197 states the use of a detergent that "has a simplified formulation" but provides no details other than it could include an enzyme system. Similarly, the following references do not disclose electrolyzed water in conjunction with an ADD composition to control hardness, dispersancy and/or corrosion. JP Application No. 10057297A describes the use of a detergent but gives no specifics. JP Application No. 10033448A also broadly describes the use of "a detergent" and "an alkaline detergent" but provides no specifics. None of the abovementioned references disclose the benefits of hardness, dispersancy and/or corrosion control when treating tableware with electrolyzed water in conjunction with a specific ADD composition, as disclosed in the present application.

There remains a need to provide a specific ADD composition and a method of using a specific ADD composition in conjunction with electrolyzed water for treating tableware in an automatic dishwashing appliance for controlling hardness, corrosion and dispersancy in order to improve cleaning, sanitizing and stain removal performance.

It has now been surprisingly discovered that using electrolyzed water in conjunction with an ADD composition comprising a halogenated salt and a builder, such as phosphate and/or silicate, completes the portfolio of cleaning chemistry that can be necessary for a robust and satisfactory automatic dishwashing end result. The present invention meets this need by providing a unique halogenated mixed oxidant cleaning system. According to this invention, superior tableware cleaning, sanitizing and stain removal can be achieved when alkalinity for bleaching/sanitization can be provided by electrolyzed water, hardness control can be provided by phosphate and anticorrosion benefits are provided by silicates.

Electrolyzed water when combined with a builder, such as a phosphate and/or silicate, in the presence of a halogenated salt, can be particularly effective in removing a wide range of soils, microorganisms, and/or stains from soiled tableware. This combination will also allow ADD compositions to be sold without bleach, a distinct advantage over the prior art, while at the same time providing the cleaning performance of a powdered automatic dishwashing detergent composition that contains both enzyme and bleach. As a result, non-bleach-containing, enzyme-based liquid-gel automatic dishwashing detergent compositions could become a consumer-preferred ADD composition.

SUMMARY OF THE INVENTION

In one aspect of the present invention, an automatic dishwashing composition for treating tableware in an automatic dishwashing appliance can comprise an electrochemical cell and/or electrolytic device for improved tableware cleaning, sanitizing, and/or stain removal, the composition comprising: (a) a halogen dioxide salt having the formula $(M)_x(XO_2)_y$, wherein X can be Cl, Br, or I and wherein M can be a metal ion or cationic entity, and wherein x and y are chosen such that the salt can be charge balanced; and (b) a component selected from the group consisting of a builder, suds suppressor, perfume, enzyme, bleach-scavenging agent, a metal-protecting agent, and mixtures thereof; wherein the composition can be optionally free of bleach.

In another aspect of the present invention, an automatic dishwashing composition for treating tableware in an automatic dishwashing appliance can comprise an electrochemical cell and/or electrolytic device for improved tableware cleaning, sanitizing, and/or stain removal, the composition comprising: (a) at least about 0.1%, by weight of the composition, of a halogenated salt having the formula $(M)_x(X)_y$, wherein X can be Cl, Br, or I and wherein M can be a metal ion or cationic entity, and wherein x and y are chosen such that the salt can be charge balanced; and (b) a component selected from the group consisting of a builder, suds suppressor, perfume, enzyme, bleach-scavenging agent, a metal-protecting agent, enzymes, and mixtures thereof; wherein the composition can be optionally free of bleach.

In another aspect of the present invention, a liquid, liquitab, and/or gel automatic dishwashing composition for treating tableware in an automatic dishwashing appliance can comprise an electrochemical cell for improved tableware cleaning, sanitizing, and/or stain removal, the composition comprising: (a) at least about 0.1%, by weight of the composition, of a halogenated salt having the formula $(M)_x(X)_y$, wherein X can be Cl, Br, or I and wherein M can be a metal ion or cationic entity, and wherein x and y are chosen such that the salt can be charge balanced; (b) a component selected from the group consisting of a builder, suds suppressor, perfume, enzyme, bleach-scavenging agent, a metal-protecting agent, and mixtures thereof; and (c) an effective amount of an enzyme; and (d) an effective amount of a thickening agent; wherein the liquid, liquitab, and/or gel composition can be optionally free of bleach.

In another aspect of the present invention, a method of treating tableware in an automatic dishwashing appliance can comprise an electrochemical cell that results in improved tableware cleaning, sanitizing, and/or stain removal, the method comprising the steps of: (a) placing tableware in need of treatment in the appliance; (b) providing an automatic dishwashing composition comprising a component selected from the group consisting of a halogenated salt, builder, suds suppressor, perfume, bleach-scavenging agent, metal-protecting agent, and mixtures thereof, during a wash and/or a rinse cycle in the appliance; (c) passing an aqueous electrolytic solution through the electrochemical cell to generate at least some electrolyzed water in the wash and/or rinse liquor of the appliance; and (d) contacting the tableware with the electrolyzed water.

In another aspect of the present invention, an article of manufacture for an automatic dishwashing appliance can comprise: (a) a package; (b) a replacement product comprising a component selected from electrolytic solution comprising halogen ions, halogenated salts having the formula $(M)_x(XO_2)_y$, and/or $(M)_x(X)_y$, wherein X can be Cl, Br, or I and wherein M can be a metal ion or cationic entity and wherein x and y are chosen such that the salt can be charge balanced, electrolysis precursor compound, a halogenated salt with low water solubility, a halogenated salt contained within a medium for controlled release, and mixtures thereof; (c) optionally, a porous basket comprising the product for dispensing; and (c) information in association with the package comprising instructions to insert the replacement components and/or the a porous basket in the appliance and/or the electrolytic device.

In yet another aspect of the present invention, an ADD composition of matter consists essentially of the in the wash and/or rinse liquor of an automatic dishwashing appliance comprising an electrochemical cell and/or electrolytic device for improved tableware cleaning, sanitizing, and/or stain removal, the composition of matter comprising: (a) at least some electrolyzed water comprising halogenated mixed oxidants; (b) an ADD composition comprising a compound selected from the group consisting of a halogenated salts, halogenated salt with low water solubility, builder, suds suppressor, perfume, enzyme, bleach-scavenging agent, a metal-protecting agent, and mixtures thereof; (c) optionally, an ADD composition comprising a compound selected from the group consisting of an electrolytic composition comprising halogen ions, an electrolytic composition comprising halogenated salts having the formula $(M)_x(XO_2)_y$, and/or $(M)_x(X)_y$, wherein X can be Cl, Br, or I and wherein M can be a metal ion or cationic entity and wherein x and y are chosen such that the salt can be charge balanced, an electrolysis precursor compound, a halogenated salt with low water solubility, an electrolysis precursor compound contained within a medium for controlled release, and mixtures thereof; and (d) optionally, at least one adjunct ingredient.

The following description can be provided to enable any person skilled in the art to make and use the invention, and can be provided in the context of a particular application and its requirements. Various modifications to the embodiments will be readily apparent to those skilled in the art, and the generic principles defined herein can be applied to other embodiments and applications without departing from the spirit and scope of the invention. The present invention can be not intended to be limited to the embodiments shown. Thus, since the following specific embodiments of the present invention are intended only to exemplify, but in no way limit, the operation of the present invention, the present invention can be to be accorded the widest scope consistent with the principles, features and teachings disclosed herein.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The various advantages of the present invention will become apparent to those skilled in the art after a study of the foregoing specification and following claims. The following specific embodiments of the present invention are intended to exemplify, but in no way limit, the operation of the present invention. All documents cited are, in relevant part, incorporated herein by reference; the citation of any document can be not to be construed as an admission that it can be prior art with respect to the present invention.

DETAILED DESCRIPTION OF THE INVENTION

Electrolysis

Electrodes

An electrode can generally have any shape that can effectively conduct electricity through the aqueous electrolytic solution between itself and another electrode, and can include, but can be not limited to, a planar electrode, an annular electrode, a spring-type electrode, and a porous electrode. The anode and cathode electrodes can be shaped and positioned to provide a substantially uniform gap between a cathode and an anode electrode pair. On the other hand, the anode and the cathode can have different shapes, different dimensions, and can be positioned apart from one another non-uniformly. The important relationship between the anode and the cathode can be for a sufficient flow of current through the anode at an appropriate voltage to promote the conversion of the halogenated salt solution to halogenated bleach species within the cell passage adjacent the anode.

Planar electrodes, such as shown, have a length along the flow path of the solution, and a width oriented transverse to the flow path. The aspect ratio of planar electrodes, defined by the ratio of the length to the width, can be generally between 0.2 and 10, more preferably between 0.1 and 6, and most preferably between 2 and 4.

Another embodiment of the present invention relates to an automatic dishwashing appliance containing a robust cell and/or device. The robust cell being non-partitioned can be less prone to fouling. The robust cell can comprise a cathode of stainless steel and an anode of titanium. The anode can be coated and/or layered with at least one of the materials selected from the group consisting of platinum, ruthenium, iridium, and oxides, alloys, and mixtures thereof. The cell passage of the robust cell forms a gap between the at least one pair of electrodes having a gap spacing between about 0.1 mm to about 0.5 mm; and wherein the operating voltage can be between about 3 and about 6 volts.

Porous media useful in the present invention are commercially available from Astro Met Inc. in Cincinnati, Ohio, Porvair Inc. in Henderson, N.C., or Mott Metallurgical in Farmington, Conn. Alternately U.S. Pat. Nos. 5,447,774 and 5,937,641 give suitable examples of porous media processing. Preferably, the porous anode, 21 a, has a ratio of surface area (in square centimeters) to total volume (in cubic centimeters) of more than about 5 $cm^{-1}$, more preferably of more than about 10 $cm^{-1}$, even more preferably more than about 50 $cm^{-1}$, and most preferably of more than about 200 $cm^{-1}$. Preferably the porous anode, 21a, has a porosity of at least about 10%, more preferably of about 30% to about 98%, and most preferably of about 40% to about 70%. Preferably, the porous anode has a combination of high surface area and electrical conductivity across the entire volume of the anode, to optimize the solution flow rate through the anode, and the conversion of halogenated salt solution contained in the solution to the halogenated bleach species.

The electrodes are commonly metallic, conductive materials, though non-metallic conducting materials, such as carbon, can also be used. The materials of the anode and the cathode can be the same, but can advantageously be different. To minimize corrosion, chemical resistant metals are preferably used. Examples of suitable electrodes are disclosed in U.S. Pat. No. 3,632,498 and U.S. Pat. No. 3,771,385. Preferred anode metals are stainless steel, platinum, palladium, iridium, ruthenium, as well as iron, nickel and chromium, and alloys and metal oxides thereof. More preferred are electrodes made of a valve metal such as titanium, tantalum, aluminum, zirconium, tungsten or alloys thereof, which are coated or layered with a Group VIII metal that can be preferably selected from platinum, iridium, and ruthenium, and oxides and alloys thereof. One preferred anode can be made of titanium core and coated with, or layered with, ruthenium, ruthenium oxide, iridium, iridium oxide, and mixtures thereof, having a thickness of at least 0.1 micron, preferably at least 0.3 micron.

For many applications, a metal foil having a thickness of about 0.03 mm to about 0.3 mm can be used. Foil electrodes should be made stable in the electrochemical cell so that they do not warp or flex in response to the flow of liquids through the passage that can interfere with proper electrolysis operation. The use of foil electrodes can be particularly advantageous when the cost of cell and/or device should be minimized, or when the lifespan of the electrolysis device can be expected or intended to be short, generally about one year or less. Foil electrodes can be made of any of the metals described above, and are preferably attached as a laminate to a less expensive electrically-conductive base metal, such as tantalum, stainless steel, and others.

The following references are also related to electrodes: U.S. Pat. No. 3,616,355; U.S. Pat. No. 4,048,047; U.S. Pat. No. 4,062,754; U.S. Pat. No. 4,100,052; U.S. Pat. No. 4,328,084; U.S. Pat. No. 4,761,208; U.S. Pat. No. 5,314,589; U.S. Pat. No. 5,395,492; U.S. Pat. No. 5,439,576; U.S. Pat. No. 5,954,939 (equiv. EP 711,730); and WO 00/34184.

Electrochemical Cell

An electrochemical cell can comprise at least one pair of electrodes; an anode, and a cathode, defining a cell gap, comprising a cell passage, formed therebetween through which the aqueous electrolytic solution can flow. The electrodes can be held a fixed distance away from one another by at least one pair of opposed non-conductive electrode holders having electrode spacers that space apart the confronting longitudinal edges of the anode and cathode defines the cell gap comprising the cell passage. The cell passage has an inlet opening through which the aqueous electrolytic solution can pass into of the electrochemical cell and an opposed outlet opening from which the effluent can pass out of the electrochemical cell.

The anode and cathode and the opposed plate holders are held tightly together between a non-conductive anode cover and cathode cover by a retaining means that can comprise non-conductive, water-proof adhesive, bolts, or other means, thereby restricting exposure of the two electrodes only to the aqueous electrolytic solution that flows through the passage. The anode lead and cathode lead extend laterally and sealably through channels made in the electrode holders.

The gap between the at least one pair of electrodes has a gap spacing between about 0.1 mm to about 5.0 mm. The operating voltage that can be applied between the at least one pair of electrodes can be between about 1 and about 12 volts; preferably between about 3 volts and 6 volts. The electrochemical cell can be disposable and/or replaceable via a refill and/or a replacement cartridge which can be removable from at least one sealed or sealable compartment of an automatic dishwashing appliance containing an attached, integrated electrochemical cell and/or electrolytic device.

The electrochemical cell can also comprise two or more anodes or two or more cathodes. The anode and cathode plates are alternated so that the anode can be confronted by a cathode on each face, with a cell passage therebetween. Examples of electrochemical cells that can comprise a plurality of anodes and cathodes are disclosed in U.S. Pat. No. 5,534,120, issued to Ando et al. on Jul. 9, 1996, and U.S. Pat. No. 4,062,754, issued to Eibl on Dec. 13, 1977, which are incorporated herein by reference.

Generally, the electrochemical cell will have at least one or more inlet openings in fluid communication with the wash and/or rinse liquor in the appliance. The cell passage can be in fluid communication with the inlet openings and at least one outlet opening which can be also in fluid communication with the wash and/or rinse liquor in the appliance.

The electrochemical cell can comprise a porous, or flow-through electrode comprising a porous cathode and a porous anode. The porous anode has a large surface area and large pore volume sufficient to pass there through a large volume of electrolytic solution. The plurality of pores and flow channels in the porous anode provide a greatly increased surface area providing a plurality of passages, through which the aqueous electrolytic solution can pass.

The flow path of the aqueous electrolytic solution through a porous anode should be sufficient, in terms of the exposure time of the solution to the surface of the anode to convert the aqueous electrolytic solution containing a halogen salt to the halogenated mixed-oxidants. The flow path can be selected to pass the aqueous electrolytic solution in parallel with the flow of electricity through the porous anode (in either the same direction or in the opposite direction to the flow of electricity), or in a cross direction with the flow of electricity. The porous anode permits a larger portion of the aqueous electrolytic solution to pass through the passages adjacent to the anode surface, thereby increasing the proportion of the halogenated salt solution that can be converted to the halogenated bleach species.

Electrolytic Solution

The components of the aqueous electrolytic solution can be selected from the group consisting of chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that the salt can be charge balanced, electrolysis precursor compounds, electrolysis salts with low water solubility, electrolysis precursor compounds contained within a medium or matrix for controlled release, and mixtures thereof.

Preferred electrolytic solutions contain at least some halogen ions, including but not limited to chloride, chlorite, bromide, bromite, iodide, and iodite, and mixtures thereof; preferably chloride ions or chlorite ions. Of course, electrolytic solutions containing higher levels of halogen ions are more efficiently converted into a discharge effluent solution having even larger amounts of the mixed oxidants. This can be due in part because the conductivity of the aqueous electrolytic solution increases with the concentration of halogen ions, thereby enabling a greater current flow across the passage gap between the pair of electrodes under a constant voltage potential. In general, to produce the same amount of mixed oxidants at a fixed power (current and voltage potential), an aqueous electrolytic solution having a higher concentration of halogen ions allows a substantially smaller gap spacing, compared to an aqueous electrolytic solution having lower concentrations of the halogen ions.

Preferably the aqueous electrolytic solution has a specific conductivity p of greater than 100 µS/cm, preferably more than 150 µS/cm, even more preferably more than 250 µS/cm, and most preferably more than 500 µS/cm.

Halogenated Mixed Oxidants

The chemistry of the conversion of halogen ions to halogenated mixed oxidants proceeds as electrical energy can be applied between the pair of electrodes and through the aqueous electrolytic solution. Since chloride in common salt can be the most prevalent halogen available, the description of the electrochemical cell chemistry and operation will be described with respect to converting chloride to chlorine, although it should be understood that other halogen ions (halides and/or halites), especially bromide, iodide, chlorite, bromite, and iodite would function and respond similarly to chloride. Similarly, since chlorinated tap water can be a useful electrolytic solution, the description below will describe the use of water having a residual amount of chloride ions, although it should be understood that other electrolytic solutions can be used, preferably those consisting of chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that the salt can be charge balanced, electrolysis precursor compounds, electrolysis salts with low water solubility, electrolysis precursor compounds contained within a medium or matrix for controlled release, and mixtures thereof.

Water containing residual amounts of chloride ions can be electrolyzed as it passes between the anode (the positively charged electrode of the pair) and the cathode (the negatively charged electrode). Two of the reactions that occur at the anode electrode are set forth below as equations 1 and 2.

$$2Cl^- \rightarrow Cl_2 + 2e^- \qquad (1)$$

$$H_2O \rightarrow \tfrac{1}{2}O_2 + 2H^+ + 2e^- \qquad (2)$$

One of the reactions that occurs at the cathode can be set forth as equation 3.

$$2H_2O + 2e^- \rightarrow H_2 + 2OH^- \qquad (3)$$

Furthermore, chlorine molecules can be converted to hypochlorous acid and hypochlorite ions as set forth in equations 4 and 5, respectively.

$$Cl_2 + H_2O \rightarrow HOCl + Cl^- + H^+ \qquad (4)$$

$$HOCl \rightarrow OCl^- + H^+ \qquad (5)$$

The chlorine gas that can be generated dissolves or diffuses into the water to generate free chlorine in the form of hypochlorous acid, hypochlorous acid ions, and hypochlorite ions. It can be believed that other various halogenated mixed oxidants that can form include chlorine dioxide ($ClO_2$), other chloro-oxides molecules, oxide molecules including ozone, hydrogen oxide ($H_2O_2$) and free radicals (oxygen singlet, hydroxyl radicals) and ions thereof. Such halogenated mixed oxidants are demonstrated and described in U.S. Pat. No. 3,616,355 and U.S. Pat. No. 4,761,208. These types of halogenated mixed oxidants are very effective biocidal agents, but have very short lifespans, lasting from a fraction of a second to minutes under ordinary, ambient conditions. Consequently, generating these biocidal agents at the point of use ensures the most effective use of the biocidal species, such as when generating the biocidal agents at specific time intervals throughout the wash and/or rinse cycles of the operation of the appliance and/or continuously without regard to sequencing.

For effective sanitizing treatment of tableware in contact with the aqueous electrolytic solution, the concentration of halogenated mixed oxidants in the electrochemical cell effluent, as measured by the DPD method, can be at least about 0.1 mg per liter (about 0.1 ppm) of electrochemical cell effluent, preferably at least about 0.2 mg per liter (about 0.2 ppm), more preferably at least about 1 mg per liter (about 1 ppm), and most preferably at least about 5 mg per liter (about 5 ppm).

An important consideration can be the productivity of the electrical power of the electrochemical cell. When battery power can be used, it can be important to provide the greatest possible production of halogenated mixed oxidants or mixed-oxidant agents for each watt of power consumed. This ensures long battery life, greater consumer convenience, smaller and more efficient electrochemical cells, and greater consumer value.

The productivity of an electrochemical cell can be expressed by equation I, $$\eta = (CCl)(Q)/(I)(V) \tag{I}$$

wherein:

$\eta$ units are micrograms of chlorine per minute, per watt of power used;

CCl can be the concentration of the generated chlorine equivalent, as determined by the DPD Method, in milligrams per liter (mg/l);

I can be the electric current in amps;

Q can be the volumetric flow rate in milliliters per minute (ml/m); and

V can be electric potential across the electrochemical cell in volts.

The productivity $\eta$ of the electroytic device used in accordance with the present invention can be typically greater than 100, and more typically greater than 250. In preferred embodiments of the electrochemical cell, the productivity $\eta$ can be more than about 500, and more preferably more than about 1000, when the aqueous electrolytic solution has a concentration of halogen ions of more than 0.001% (10 ppm) and less than 0.1%. Preferably, the cell and/or device has the above-described efficiencies when the electric current can be between about 100 milliamps and about 2000 milliamps, with typical current densities of between about 5 milliamps/cm$^2$ and 100 milliamps/cm$^2$ of exposed anode electrode surface, and more preferably between about 10 milliamps and 50 milliamps/cm$^2$. Since the electrical potentials required to convert chloride to chlorine can be about 1.36V, a voltage potential greater than 1.36V across the passage will generate a proportionally greater amount of halogenated mixed oxidants from the chloride ions.

The voltage potential maintained between any pair of anode and cathode electrodes should be generally greater than 1.36V, and generally less than about 12 volts, and can be preferably between about 2.0V and 6V, and more preferably between about 3V and 4.5V. For self-powered self-contained devices, batteries are the preferred electrical current sources. To achieve the extended life from a set of batteries, cell and/or device can be preferably designed to draw a total power of 20 watts or less, preferably 5 watts or less, more preferably 2.5 watts or less, and most preferably 1 watt or less, across the electrode pairs of the electrochemical cell.

Generally, the electrochemical cell has a cell gap spacing greater than about 0.05 mm, preferably greater than 0.10 mm, more preferably greater than about 0.15 mm, and most preferably greater than about 0.20 mm, and a cell gap spacing less than about 5 mm, preferably less than about 2.0 mm, more preferably less than about 0.80 mm, and most preferably less than about 0.50 mm. The more preferable cell gap spacings are for use with electrolytic solutions that contain a concentration of halide ions of less than about 200 ppm, and a specific conductivity $\rho$ of greater than about 250 $\mu$S/cm.

The residence time between the inlet and outlet of the anode and cathode pair can be generally less than 10 seconds and preferably can be less than 5 seconds, in more preferred embodiments, between about 0.01 seconds and about 1.5 seconds, and most preferably between 0.05 and about 0.5 seconds. The residence time can be approximated by dividing the total volume of the passage between the anode and cathode pair by the average flow rate of water through the electrochemical cell.

Operation and effectiveness of the cell and/or device requires that the aqueous electrolytic solution passes through the electrochemical cell in a quantity sufficient to generate an effective production of the halogenated mixed oxidants for the intended purpose. In general, without some means of moving the aqueous electrolytic solution through the electrochemical cell, as opposed to just filling the electrochemical cell, low levels of the halogenated mixed oxidants will be produced. Electrolytic solution comprising wash and/or rinse liquor can be moved through the cell and/or device by pumping through the electrochemical cell via an internal and/or external pumping means. Alternatively, cell and/or device can be placed into an area of the appliance washing basin where there can be water flow sufficient to pass through the electrochemical cell by gravity flow.

The following U.S. patents disclose electrochemical cells: U.S. Pat. No. 5,932,171; U.S. Pat. No. 4,481,086; U.S. Pat. No. 4,434,629; U.S. Pat. No. 4,493,760; U.S. Pat. No. 4,402,197; U.S. Pat. No. 5,250,160; U.S. Pat. No. 5,534,120; U.S. Pat. No. 5,947,135; JP Application No. 10057297A; JP Application No. 10179489A; JP Application No. 10033448A; JP Patent No. 09122060; JP Patent No. 2000116587; JP Patent No. 10178491; and EP Application No. 0983806A1.

Composition

Electrolyzed water when combined with a specific ADD composition, such as a phosphate and/or silicate in the presence of a halogenated salt, can be particularly effective in removing a wide range of soils, microorganisms, and/or stains from soiled tableware.

(a) Halogenated Salt

The present invention can comprise one or more halogenated salts selected from the group consisting of halite salt, halide salt, and mixtures thereof. The level of halogenated salt comprised in the wash and/or rinse liquor can be selected based on the required bleaching or disinfection required by the halogenated mixed oxidants, in addition to the conversion efficiency of the electrochemical cell to convert the halogenated salt to the halogenated mixed oxidants. The level of halogenated salt can be generally from about 1 ppm to about 10,000 ppm. For disinfection of wash and/or rinse liquor, a halogenated salt level can be preferably from about 1 ppm to about 5000 ppm, and more preferably about 10 ppm to about 1000 ppm. The resulting halogenated mixed-oxidant level can be from about 0.1 ppm to about 10,000 ppm, preferably from about 1 ppm to about 200 ppm. For bleaching purposes, a halogenated salt level of from about 100 ppm to about 10,000 ppm can be preferred.

The range of halogenated mixed oxidants conversion that can be achievable in the electrochemical cells of the present invention generally ranges from less than about 1% to about 99%. The level of conversion can be dependent most significantly on the design of the electrochemical cell, herein described, as well as on the electrical current properties used in the electrochemical cell.

In certain circumstances, halogenated salts of calcium and magnesium having a reduced solubility in water, as compared to sodium halogenated salts, control the rate of dissolution of the halogenated salt. The ADD composition can also be formulated with other organic and inorganic materials to control the rate of dissolution of the halogenated salt. Preferred can be a slow dissolving salt particle and/or tablet, to release sufficient halogenated salt to form an effective amount of halogenated precursor product. The release amount of the halogenated salt can be typically, between 1 milligram to 10 grams halogenated salt, for each liter of solution passed through the electrochemical cell. The ADD composition can comprise a simple admixture of the halogenated salt with the dissolution control materials, which can be selected from various well-known encapsulating materials, including but not limited to fatty alcohol, fatty acids, and waxes.

The ADD composition of the present invention can comprise a local source of halogenated salt, and a means for delivering the halogenated salt to the wash and/or rinse liquor. This embodiment can be advantageously used in those situations when the target water to be treated with the electrochemical cell does not contain a sufficient amount, or any, of the halogenated salt. The local source of halogenated salt can be released into a stream of the aqueous solution, which then ultimately passes through the electrochemical cell. The local source of halogenated salt can also be released into at least some of the wash and/or rinse liquor present in the washing basin of the automatic dishwashing appliance, which portion can be then drawn into the electrochemical cell. Preferably, in order to maximize the conversion to halogenated mixed oxidants, and limit the addition of salts to the wash and/or rinse liquor, generally all the local source of halogenated salt passes through the electrochemical cell. The local source of halogenated salt can also supplement any residual levels of halogenated salt already contained in incoming tap water and/or the wash and/or rinse liquor.

The local source of halogen ions can be from an ADD composition and/or rinse aid composition, a concentrated brine solution, a halogenated salt tablet, granule, or pellet in fluid contact with the aqueous electrolytic solution, or in a porous basket hanging on the rack of the automatic dishwashing appliance, or both. A preferred localized source of halogen ions can be a solid form, such as a pill or tablet, of halide salt, such as sodium chloride (common salt) or sodium chlorite. The means for delivering the local source of halogen ions can comprise a salt chamber or a porous basket comprising the halogenated salt, preferably a pill of tablet, through which at least some of the aqueous electrolytic solution will pass, thereby dissolving at least some of the halide salt into the portion of water. The salted portion of water then ultimately passes into the electrochemical cell. The salt chamber or a porous basket can comprise a salt void that can be formed in the body and positioned in fluid communication with the portion of water that will pass through the electrochemical cell.

One embodiment of the present invention relates to an ADD composition, wherein the halogenated salt can be in a form selected from the group characterized by low water solubility, contained within a medium for controlled release, and combinations thereof.

Another embodiment of the present invention relates to an ADD composition, wherein the controlled release form provides a local source of the halogenated salt comprising a form such that once placed inside a dishwashing appliance it provides a controlled release of steady levels of halogen dioxide salts into the wash and/or rinse liquors during operation of an automatic dishwasher over a period of from 1 day to 365 days of regular household and/or commercial use.

(i) Halogen Dioxide Salt—The precursor material from which halogen dioxide can be formed can be referred to as a halogen dioxide salt. The halogen dioxide salt of the present invention having the formula $(M)_x(XO_2)_y$, wherein X can be Cl, Br, or I and wherein M can be a metal ion or cationic entity, and wherein x and y are chosen such that the salt can be charge balanced. The halogen dioxide salt can comprise two or more salts in various mixtures.

The most preferred halite salt can be sodium chlorite. Sodium chlorite can be not a salt ordinarily found in tap water, well water, and other water sources. Consequently, an amount of the sodium chlorite salt can be added into the wash and/or rinse liquor at a desired concentration generally of at least about 0.1 ppm.

The wash and/or rinse liquor can comprise substantially no chloride ($Cl^-$) or other halide ions, which upon electrolysis can form a mixed oxidant, including hypochlorite. Preferably, electrolyzed discharge effluent can comprise less than about 1.0 ppm, and more preferably less than 0.1 ppm, of chlorine. The wash and/or rinse liquor comprising the sodium chlorite can be provided in a variety of ways.

One embodiment of the present invention relates to an ADD composition comprising sodium chlorite, preferably, a concentrated solution about 2% to about 35% sodium chlorite by weight of the composition in the form of a liquid, liquitab, and/or gel.

One embodiment of the present invention relates to an automatic dishwashing composition for treating tableware in an automatic dishwashing appliance comprising an electrochemical cell and/or electrolytic device for improved tableware cleaning, sanitizing, and/or stain removal, the composition comprising: (a) a halogen dioxide salt having the formula $(M)_x(XO_2)_y$, wherein X can be Cl, Br, or I and wherein M can be a metal ion or cationic entity, and wherein x and y are chosen such that the salt can be charge balanced; and (b) a component selected from the group consisting of a builder, suds suppressor, perfume, enzyme, bleach-scavenging agent, a metal-protecting agent, and mixtures thereof; wherein the composition can be optionally free of bleach.

Another embodiment of the present invention relates to an ADD composition, wherein the halogenated salt can comprise a salt selected from the group consisting of $NaClO_2$, $KClO_2$, and mixtures thereof. Another embodiment of the present invention relates to an ADD composition, wherein $NaClO_2$, $KClO_2$, and mixtures thereof, can be present at a level of greater than about 0.1%, preferably at a level greater than about 0.5%, more preferably at a level of greater than about 1.0% by weight of the composition, and most preferably at a level of greater than about 2%, by weight of the composition.

(ii) Other Halogenated Salts—In substitution of and/or addition to halogen dioxide salt, the present invention can comprise one or more halide salts. The halide salt of the present invention having the formula $(M)_x(X)_y$, wherein X can be Cl, Br, or I and wherein M can be a metal ion or cationic entity, and wherein x and y are chosen such that the salt can be charge balanced, can be used to enhance the disinfection and bleaching performance of the effluent that can be discharged from the electrochemical cell, or to provide other halogenated mixed oxidants, when preferred, in response to the passing of electrical current through the electrochemical cell.

One embodiment of the present invention relates to an automatic dishwashing composition for treating tableware in an automatic dishwashing appliance comprising an electrochemical cell and/or electrolytic device for improved tableware cleaning, sanitizing, and/or stain removal, the composition comprising: (a) at least about 0.1%, by weight of the composition, of a halogenated salt having the formula $(M)_x(X)_y$, wherein X can be Cl, Br, or I and wherein M can be a metal ion or cationic entity, and wherein x and y are chosen such that the salt can be charge balanced; and (b) a component selected from the group consisting of a builder, suds suppressor, perfume, enzyme, bleach-scavenging agent, a metal-protecting agent, enzymes, and mixtures thereof; wherein the composition can be optionally free of bleach.

Another embodiment of the present invention relates to an ADD composition comprising NaCl, KCl, and mixtures thereof, at a level of greater than about 0.1%, preferably at a level greater than about 0.5% by weight of the composition, more preferably at a level of greater than about 1% by weight of the composition. most preferably at a level of greater than about 2%, by weight of the composition.

(b) Builders

Detergent builders are included in the compositions herein to assist in controlling mineral hardness and dispersancy. Inorganic as well as organic builders can be used. Builders are typically used in automatic dishwashing, for example to assist in the removal of particulate soils. The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Lower or higher levels of builder, however, are not meant to be excluded.

One embodiment of the present invention relates to an ADD composition, wherein the builder can be selected from the group consisting of phosphate, phosphate oligomers or polymers and salts thereof, silicate oligomers or polymers and salts thereof, aluminosilicates, magnesioaluminosiliates, citrate, and mixtures thereof.

(i) Phosphate Builders—Phosphate detergent builders for use in ADD compositions are well known. They include, but are not limited to, the alkali metal, ammonium and alkanolammonium salts of polyphosphates (exemplified by the tripolyphosphates, pyrophosphates, and glassy polymeric meta-phosphates). Phosphate builder sources are described in detail in Kirk Othmer, 3rd Edition, Vol. 17, pp. 426-472 and in "Advanced Inorganic Chemistry" by Cotton and Wilkinson, pp. 394-400 (John Wiley and Sons, Inc.; 1972).

Inorganic or non-phosphate P-containing detergent builders include, but are not limited to, phosphonates, phytic acid, silicates, carbonates (including bicarbonates and sesquicarbonates), sulfates, citrate, zeolite or layered silicate, and aluminosilicates. See U.S. Pat. No. 4,605,509 for examples of preferred aluminosilicates.

(ii) Silicate Builders—The present automatic dishwashing detergent compositions can further comprise water-soluble silicates. Water-soluble silicates herein are any silicates which are soluble to the extent that they do not adversely affect spotting/filming characteristics of the ADD composition.

Examples of silicates are sodium metasilicate and, more generally, the alkali metal silicates, particularly those having a $SiO_2:Na_2O$ ratio in the range 1.6:1 to 3.2:1; and layered silicates, such as the layered sodium silicates described in U.S. Pat. No. 4,664,839, issued can 12, 1987 to H. P. Rieck. NaSKS-6® can be a crystalline layered silicate marketed by Hoechst (commonly abbreviated herein as "SKS-6"). Unlike zeolite builders, Na SKS-6 and other water-soluble silicates useful herein do not contain aluminum. NaSKS-6 can be the $\delta$-$Na_2SiO_5$ form of layered silicate and can be prepared by methods such as those described in German DE-A-3,417,649 and DE-A-3,742,043. SKS-6 can be a preferred layered silicate for use herein, but other such layered silicates, such as those having the general formula $NaMSi_xO_{2x+1}.yH_2O$ wherein M can be sodium or hydrogen, x can be a number from 1.9 to 4, preferably 2, and y can be a number from 0 to 20, preferably 0 can be used. Various other layered silicates from Hoechst include NaSKS-5, NaSKS-7 and NaSKS-11, as the $\alpha$-, $\beta$- and $\gamma$-forms. Other silicates can also be useful, such as for example magnesium silicate, which can serve as a crispening agent in granular formulations, as a stabilizing agent for oxygen bleaches, and as a component of suds control systems.

Silicates particularly useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates can be used in an ADD context to boost wash pH to a desired level.

Aluminosilicate builders can be used in the present compositions though are not preferred for automatic dishwashing detergents. Aluminosilicate builders are of great importance in most currently marketed heavy duty granular detergent compositions, and can also be a significant builder ingredient in liquid detergent formulations. Aluminosilicate builders include those having the empirical formula: $Na_2O.Al_2O_3.xSiO_z.yH_2O$ wherein z and y are integers of at least about 6, the molar ratio of z to y can be in the range from 1.0 to about 0.5, and x can be an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials can be disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In another embodiment, the crystalline aluminosilicate ion exchange material has the formula: $Na_{12}[(AlO_2)_{12}(SiO_2)_{12}].xH_2O$ wherein x can be from about 20 to about 30, especially about 27. This material can be known as Zeolite A. Dehydrated zeolites (x=0-10) can also be used herein. Preferably, the aluminosilicate has a particle size of about 0.1-10 microns in diameter. Individual particles can desirably be even smaller than 0.1 micron to further assist kinetics of exchange through maximization of surface area. High surface area also increases utility of aluminosilicates as adsorbents for surfactants, especially in granular compositions. Aggregates of silicate or aluminosilicate particles can be useful, a single aggregate having dimensions tailored to minimize segregation in granular compositions, while the aggregate particle remains dispersible to submicron individual particles during the wash. As with other builders such as carbonates, it can be desirable to use zeolites in any physical or morphological form adapted to promote surfactant carrier function, and appropriate particle sizes can be freely selected by the formulator.

(iii) Carbonate Builders—Examples of carbonate builders are the alkaline earth and alkali metal carbonates as disclosed in German Patent Application No. 2,321,001 published on Nov. 15, 1973. Various grades and types of sodium carbonate and sodium sesquicarbonate can be used, certain of which are particularly useful as carriers for other ingredients, especially detersive surfactants.

(iv) Organic Detergent Builders—Organic detergent builders suitable for the purposes of the present invention include, but are not restricted to, a wide variety of polycarboxylate compounds. As used herein, "polycarboxylate" refers to compounds having a plurality of carboxylate groups, preferably at least about 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on can 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

(v) Other Useful Builders—Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty laundry detergent and automatic dishwashing formulations due to their availability from renewable resources and their biodegradability. Citrates can also be used in combination with zeolite, the aforementioned BRITESIL types, and/or layered silicate builders. Oxydisuccinates are also useful in such compositions and combinations.

Also suitable in the detergent compositions of the present invention are the 3,3-dicarboxy-4-oxa-1,6-hexanedionates and the related compounds disclosed in U.S. Pat. No. 4,566,984, Bush, issued Jan. 28, 1986. Useful succinic acid builders include the $C_5$-$C_{20}$ alkyl and alkenyl succinic acids and salts thereof. A particularly preferred compound of this type can be dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Where phosphorus-based builders can be used, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used though such materials are more commonly used in a low-level mode as chelants or stabilizers.

Fatty acids, e.g., $C_{12}$-$C_{18}$ monocarboxylic acids, can also be incorporated into the compositions alone, or in combination with the aforethe builders, especially citrate and/or the succinate builders, to provide additional builder activity but are generally not desired. Such use of fatty acids will generally result in a diminution of sudsing in laundry compositions, which can need to be taken into account by the formulator. Fatty acids or their salts are undesirable in Automatic Dishwashing (ADD) embodiments in situations wherein soap scums can form and be deposited on dishware.

(c) Suds Suppressor

The ADD compositions of the present invention can optionally contain an alkyl phosphate ester suds suppressor, a silicone suds suppressor, or combinations thereof. Levels in general are from 0% to about 10%, preferably, from about 0.001% to about 5%. However, generally (for cost and/or deposition considerations) preferred compositions herein do not comprise suds suppressors or comprise suds suppressors only at low levels, e.g., less than about 0.1% of active suds suppressing agent.

Silicone suds suppressor technology and other defoaming agents useful herein are extensively documented in "Defoaming, Theory and Industrial Applications", Ed., P. R. Garrett, Marcel Dekker, N.Y., 1973, ISBN 0-8247-8770-6, incorporated herein by reference. See especially the chapters entitled "Foam control in Detergent Products" (Ferch et al) and "Surfactant Antifoams" (Blease et al). See also U.S. Pat. Nos. 3,933,672 and 4,136,045. Highly preferred silicone suds suppressors are the compounded types known for use in laundry detergents such as heavy-duty granules, although types hitherto used only in heavy-duty liquid detergents can also be incorporated in the instant compositions. For example, polydimethylsiloxanes having trimethylsilyl or alternate end-blocking units can be used as the silicone. These can be compounded with silica and/or with surface-active non-silicon components, as illustrated by a suds suppressor comprising 12% silicone/silica, 18% stearyl alcohol and 70% starch in granular form. A suitable commercial source of the silicone active compounds can be Dow Corning Corp.

If it can be desired to use a phosphate ester, suitable compounds are disclosed in U.S. Pat. No. 3,314,891, issued Apr. 18, 1967, to Schmolka et al, incorporated herein by reference. Preferred alkyl phosphate esters contain from 16-20 carbon atoms. Highly preferred alkyl phosphate esters are monostearyl acid phosphate or monooleyl acid phosphate, or salts thereof, particularly alkali metal salts, or mixtures thereof.

It has been found preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

One embodiment of the present invention relates to an ADD composition, wherein the suds suppressor can be selected from the group consisting of low-foaming nonionic surfactants, low-foaming nonionic surfactants with a cloud point below about 30° C., alkoxylates or mixed alkoxylates of linear fatty alcohols, alkoxylates or mixed alkoxylates of alkylphenols, block co-polymers of ethylene and propylene glycol, $C_{9/11}EO_8$-cyclohexyl acetal alkyl capped nonionic, $C_{11}EO_7$-n-butyl acetal, $C_{9/11}EO_8$-2-ethylhexyl acetal, $C_{11}EO_8$-pyranyl, alcohol alkoxylate, and mixtures thereof.

(d) Perfume (i) Non-Blooming Perfumes—Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Non-limiting examples of perfume ingredients useful herein include: 7-acetyl-1,2,3,4,5,6,7,8-octahydro-1,1,6,7-tetramethyl naphthalene; ionone methyl; ionone gamma methyl; methyl cedrylone; methyl dihydrojasmonate; methyl 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; para-hydroxy-phenyl-butanone; benzophenone; methyl beta-naphthyl ketone; 6-acetyl-1,1,2,3,3,5-hexamethyl indane; 5-acetyl-3-isopropyl-1,1,2,6-tetramethyl indane; 1-dodecanal, 4-(4-hydroxy-4-methylpentyl)-3-cyclohexene-1-carboxaldehyde; 7-hydroxy-3,7-dimethyl ocatanal; 10-undecen-1-al; iso-hexenyl cyclohexyl carboxaldehyde; formyl tricyclodecane; condensation products of hydroxycitronellal and methyl anthranilate, condensation products of hydroxycitronellal and indol, condensation products of phenyl acetaldehyde and indol; 2-methyl-3-(para-tert-butylphenyl)-propionaldehyde; ethyl vanillin; heliotropin; hexyl cinnamic aldehyde; amyl cinnamic aldehyde; 2-methyl-2-(para-iso-propylphenyl)-propionaldehyde; coumarin; decalactone gamma; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; beta-naphthol methyl ether; ambroxane; dodecahydro-3a,6,6,9a-tetramethylnaphtho[2,1b]furan; cedrol, 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; tricyclodecenyl propionate; tricyclodecenyl acetate; benzyl salicylate; cedryl acetate; and para-(tert-butyl)cyclohexyl acetate.

Particularly preferred perfume materials are those that provide the largest odor improvements in finished product compositions containing cellulases. These perfumes include but are not limited to: hexyl cinnamic aldehyde; 2-methyl-3-(para-tert-butylphenyl)-propionaldehyde; 7-acetyl-1,2,3,4,5, 6,7,8-octahydro-1,1,6,7-tetramethyl naphthalene; benzyl salicylate; 7-acetyl-1,1,3,4,4,6-hexamethyl tetralin; para-tert-butyl cyclohexyl acetate; methyl dihydro jasmonate; beta-napthol methyl ether; methyl beta-naphthyl ketone; 2-methyl-2-(para-iso-propylphenyl)-propionaldehyde; 1,3, 4,6,7,8-hexahydro-4,6,6,7,8,8-hexamethyl-cyclopenta-gamma-2-benzopyrane; dodecahydro-3a,6,6,9a-tetramethyl-naphtho[2,1b]furan; anisaldehyde; coumarin; cedrol; vanillin; cyclopentadecanolide; tricyclodecenyl acetate; and tricyclodecenyl propionate.

Other perfume materials include essential oils, resinoids, and resins from a variety of sources including, but not limited to: Peru balsam, Olibanum resinoid, *styrax*, labdanum resin, nutmeg, *cassia* oil, benzoin resin, coriander and lavandin. Still other perfume chemicals include phenyl ethyl alcohol, terpineol, linalool, linalyl acetate, geraniol, nerol, 2-(1,1-dimethylethyl)-cyclohexanol acetate, benzyl acetate, and eugenol. Carriers such as diethylphthalate can be used in the finished perfume compositions.

(ii) Blooming Perfumes—Blooming perfume compositions, as disclosed herein, can be formulated into automatic dishwashing detergent compositions and provide significantly better noticeability to the consumer than non-blooming perfume compositions not containing a substantial amount of blooming perfume ingredients. Additionally, residual perfume can be not desirable on many surfaces, including dishes, glasses and cutlery, especially those made of plastic, rubber and silicone.

A blooming perfume ingredient can be characterized by its boiling point (B.P.) and its octanol/water partition coefficient (P). The octanol/water partition coefficient of a perfume ingredient can be the ratio between its equilibrium concentrations in octanol and in water. The preferred perfume ingredients of this invention have a B.P., determined at the normal, standard pressure of about 760 mm Hg, of about 260° C. or lower, preferably less than about 255° C.; and more preferably less than about 250° C., and an octanol/water partition coefficient P of about 1,000 or higher. Since the partition coefficients of the preferred perfume ingredients of this invention have high values, they are more conveniently given in the form of their logarithm to the base 10, logP. Thus the preferred perfume ingredients of this invention have logP at □□□ C. of about 3 or higher.

One embodiment of the present invention relates to an ADD composition, wherein the perfume can be from about 0.01% to about 5%, by weight, a blooming perfume composition, wherein the blooming perfume composition can comprise from about 50% to about 99% of blooming perfume ingredients having a boiling point of less than about 260° C. and a ClogP of at least about 3, and wherein the blooming perfume composition comprising at least about 5 different blooming perfume ingredients, and from about 0.5% to about 10% of base masking perfume ingredients having a boiling point of more than about 260° C. and a ClogP of at least about 3.

The following U.S. patents disclose perfumes: U.S. Pat. No. 6,143,707; U.S. Pat. No. 6,228,821; U.S. Pat. No. 5,929, 022; and U.S. Pat. No. 5,670,466.

(e) Bleach-Scavenging Agent

Additionally, from 0% to about 10%, preferably from about 0.01% to about 6% by weight, of bleach-scavengers can be added to compositions of the present invention to prevent chlorine and/or oxygen bleach species present in the wash and/or rinse liquor from attacking and inactivating the enzymes, especially under alkaline washing conditions. While chlorine levels in tap water can be small, typically in the range from about 0.5 ppm to about 1.75 ppm, the available chlorine in the total volume of water that comes in contact with the enzyme during dishwashing can be usually large; accordingly, enzyme stability in-use can be problematic.

Suitable bleach-scavenger anions are salts containing ammonium cations. These can be selected from the group consisting of reducing materials like sulfite, bisulfite, thiosulfite, thiosulfate, iodide, etc., antioxidants like carbonate, ascorbate, etc., organic amines such as ethylenediaminetetracetic acid (EDTA) or alkali metal salt thereof and monoethanolamine (MEA), and mixtures thereof. Other conventional scavenging anions like sulfate, bisulfate, carbonate, bicarbonate, percarbonate, nitrate, chloride, borate, sodium perborate tetrahydrate, sodium perborate monohydrate, percarbonate, phosphate, condensed phosphate, acetate, benzoate, citrate, formate, lactate, malate, tartrate, salicylate, etc. and mixtures thereof can also be used.

One embodiment of the present invention relates to a bleach-scavenging agent selected from the group consisting of perborate, percarbonate, ascorbic acid or derivatives thereof, carbamate, ammonium, sulfite, bisulfite, aluminum tristearate, sodium silicate, benzotriazole, amines, amino acids, and mixtures thereof. Another embodiment of the present invention relates to an ADD composition that does not contain chlorine bleach, oxygen bleach, and mixtures thereof.

(f) Metal-Protecting Agent

The present ADD compositions can contain one or more material care agents which are effective as corrosion inhibitors and/or anti-tarnish aids. Such materials are preferred components of machine dishwashing compositions especially in certain European countries where the use of electroplated nickel silver and sterling silver can be still comparatively common in domestic flatware, or when aluminium protection can be a concern and the composition can be low in silicate. Generally, such material care agents include metasilicate, silicate, bismuth salts, manganese salts, paraffin, triazoles, pyrazoles, thiols, mercaptans, aluminium fatty acid salts, and mixtures thereof.

When present, such protecting materials are preferably incorporated at low levels, e.g., from about 0.01% to about 5% of the ADD composition. Suitable corrosion inhibitors include paraffin oil, typically a predominantly branched aliphatic hydrocarbon having a number of carbon atoms in the range of from about 20 to about 50; preferred paraffin oil can be selected from predominantly branched $C_{25-45}$ species with a ratio of cyclic to noncyclic hydrocarbons of about 32:68. A paraffin oil meeting those characteristics can be sold by Wintershall, Salzbergen, Germany, under the trade name WINOG 70. Additionally, the addition of low levels of bismuth nitrate (i.e., $Bi(NO_3)_3$) can be also preferred.

Other corrosion inhibitor compounds include benzotriazole and comparable compounds; mercaptans or thiols including thionaphtol and thioanthranol; and finely divided Aluminium fatty acid salts, such as aluminium tristearate. The formulator will recognize that such materials will generally be used judiciously and in limited quantities so as to avoid any tendency to produce spots or films on glassware or to compromise the bleaching action of the compositions. For this reason, mercaptan anti-tarnishes which are quite strongly bleach-reactive and common fatty carboxylic acids which precipitate with calcium in particular are preferably avoided.

One embodiment of the present invention relates to a metal-protecting agent selected from the group consisting of perborate, percarbonate, ascorbic acid or derivatives thereof, carbamate, ammonium, sulfite, bisulfite, aluminum tristearate, sodium silicate, benzotriazole, amines, amino acids, and mixtures thereof.

Adjunct Ingredients

Detersive ingredients or adjuncts optionally included in the instant ADD compositions can include one or more materials for assisting or enhancing cleaning, sanitizing and stain removal performance of tableware treated by electrolyzed water in an automatic dishwashing appliance containing an electrochemical cell and/or electrolytic device. They are further selected based on the form of the composition, i.e., whether the composition can be to be sold as a liquid, paste (semi-solid), or solid form (including tablets and the preferred granular forms for the present compositions).

Adjuncts which can also be included in compositions of the present invention, at their conventional art-established levels for use (generally, adjunct materials comprise, in total, from about 1% to about 90%, preferably from about 5% to about 75%, more preferably from about 10% to about 50%, by weight of the compositions), and can include other active ingredients such as nanoparticles, functionalized surface molecules, polymers, surfactants, co-surfactants, metal ions, proteins, dyes, acids, bases, organic solvents, enzymes, enzyme stabilizing systems, chelants, optical brighteners, soil release agents, wetting agents, dispersants, blooming perfumes, colorants, filler salts, hydrotropes, perservatives, anti-oxidants, germicides, fungicides, color speckles, silvercare, anti-tarnishing agents, alkalinity sources, solubilizing agents, carriers, electrode maintenance and/or descaling agents, processing aids, pigments, and pH control agents, bleaching agent, bleach activators, bleach catalysts and mixtures thereof. These adjuncts are described in detail in U.S. Pat. No. 6,143,707, Trinh et al., incorporated herein by reference.

The precise nature of these additional detergent ingredients, and levels of incorporation thereof, will depend on the physical form of the composition and the nature of the operation for which the composition can be to be used. The selection of the adjunct will depend upon the type and use of the composition. Non-limiting illustrative examples of compositions as well as suitable adjunct(s) for the illustrative compositions are described hereinafter. Particularly preferred adjuncts are surfactants, enzymes, chelants, dispersant polymers, thickeners, and pH adjusting agents as described in detail hereinafter.

(a) Surfactant

One embodiment of the present invention relates to an ADD composition comprising a surfactant can be selected from the group consisting of anionic surfactants, cationic surfactants, nonionic surfactants, amphoteric surfactants, ampholytic surfactants, zwitterionic surfactants, and mixtures thereof.

It should be noted that low foaming nonionic surfactants are useful in automatic dishwashing to assist cleaning, help defoam food soil foams, especially from proteins, and to help control spotting/filming and are desirably included in the present detergent compositions at levels of from about 0.1% to about 20%, preferably from about 0.5% to about 5%, by weight of the composition. In general, bleach-stable surfactants are preferred. ADD compositions of the present invention preferably comprise low foaming nonionic surfactants (LFNIs).

LFNIs are most typically used in ADDs on account of the improved water-sheeting action (especially from glass) which they confer to the ADD composition. They also encompass non-silicone, nonphosphate polymeric materials further illustrated hereinafter which are known to defoam food soils encountered in automatic dishwashing.

Preferred LFNIs include nonionic alkoxylated surfactants, especially ethoxylates derived from primary alcohols, and blends thereof with more sophisticated surfactants, such as the polyoxypropylene/polyoxyethylene/polyoxypropylene (PO/EO/PO) reverse block polymers. The PO/EO/PO polymer-type surfactants are well-known to have foam suppressing or defoaming action, especially in relation to common food soil ingredients such as egg.

In a preferred embodiment, the LFNI can be an ethoxylated surfactant derived from the reaction of a monohydroxy alcohol or alkylphenol containing from about 8 to about 20 carbon atoms, with from about 6 to about 15 moles of ethylene oxide per mole of alcohol or alkyl phenol on an average basis.

A particularly preferred LFNI can be derived from a straight chain fatty alcohol containing from about 16 to about 20 carbon atoms ($C_{16}$-$C_{20}$ alcohol), preferably a $C_{18}$ alcohol, condensed with an average of from about 6 to about 15 moles, preferably from about 7 to about 12 moles, and most preferably from about 7 to about 9 moles of ethylene oxide per mole of alcohol. Preferably the ethoxylated nonionic surfactant so derived has a narrow ethoxylate distribution relative to the average.

The LFNI can optionally contain propylene oxide in an amount up to about 15% by weight. Other preferred LFNI surfactants can be prepared by the processes described in U.S. Pat. No. 4,223,163, issued Sep. 16, 1980, Builloty, incorporated herein by reference.

Highly preferred ADDs herein wherein the LFNI can be present make use of ethoxylated monohydroxy alcohol or alkyl phenol and additionally comprise a polyoxyethylene, polyoxypropylene block polymeric compound; the ethoxylated monohydroxy alcohol or alkyl phenol fraction of the LFNI comprising from about 20% to about 100%, preferably from about 30% to about 70%, of the total LFNI.

Suitable block polyoxyethylene-polyoxypropylene polymeric compounds that meet the requirements described hereinbefore include those based on ethylene glycol, propylene glycol, glycerol, trimethylolpropane and ethylenediamine as initiator reactive hydrogen compound. Polymeric compounds made from a sequential ethoxylation and propoxylation of initiator compounds with a single reactive hydrogen atom, such as $C_{12-18}$ aliphatic alcohols, do not generally provide satisfactory suds control in the instant ADDs. Certain of the block polymer surfactant compounds designated PLURONIC® and TETRONIC® by the BASF-Wyandotte Corp., Wyandotte, Mich., are suitable in ADD compositions of the invention.

A particularly preferred LFNI contains from about 40% to about 70% of a polyoxypropylene/polyoxyethylene/polyoxypropylene block polymer blend comprising about 75%, by weight of the blend, of a reverse block co-polymer of polyoxyethylene and polyoxypropylene containing 17 moles of ethylene oxide and 44 moles of propylene oxide; and about 25%, by weight of the blend, of a block co-polymer of polyoxyethylene and polyoxypropylene initiated with trimethylolpropane and containing 99 moles of propylene oxide and 24 moles of ethylene oxide per mole of trimethylolpropane.

Suitable for use as LFNI in the ADD compositions are those LFNI having relatively low cloud points and high hydrophilic-lipophilic balance (HLB). Cloud points of 1% solutions in water are typically below about 32° C. and preferably lower, e.g., 0° C., for optimum control of sudsing throughout a full range of water temperatures.

LFNIs which can also be used include a $C_{18}$ alcohol polyethoxylate, having a degree of ethoxylation of about 8, commercially available as SLF18 from Olin Corp., and any biodegradable LFNI having the melting point properties discussed hereinabove.

(b) Co-Surfactant

The composition of the present invention can further contain optional co-surfactants. These optional surfactants will be preferably bleach stable. Preferred optional co-surfactants are low cloud point nonionic surfactants, high cloud point nonionic surfactants, anionic surfactants and mixtures thereof.

Nonionic co-surfactants useful in the present invention Automatic Dishwashing compositions are when present desirably included in the present detergent compositions at levels of from about 0.1% to about 15% of the composition. In general, bleach-stable co-surfactants are preferred. Nonionic surfactants generally are well known, being described in more detail in Kirk Othmer's Encyclopedia of Chemical Technology, 3rd Ed., Vol. 22, pp. 360-379, "Surfactants and Detersive Systems".

"Cloud point", as used herein, can be a well known property of nonionic surfactants which can be the result of the surfactant becoming less soluble with increasing temperature, the temperature at which the appearance of a second phase can be observable can be referred to as the "cloud point" (See Kirk Othmer, pp. 360-362, hereinbefore).

As used herein, a "low cloud point nonionic co-surfactant" can be defined as a nonionic surfactant system ingredient having a cloud point of less than 30□ C., preferably less than about 20□ C., and most preferably less than about 10□ C. Typical low cloud point nonionic co-surfactants include nonionic alkoxylated surfactants, especially ethoxylates derived from primary alcohol, and polyoxypropylene/polyoxyethylene/polyoxypropylene (PO/EO/PO) reverse block polymers. Also, such low cloud point nonionic co-surfactants include, for example, ethoxylated-propoxylated alcohol (e.g., Olin Corporation's Poly-Tergent® SLF18) and epoxy-capped poly(oxyalkylated) alcohols (e.g., Olin Corporation's Poly-Tergent® SLF18B series of nonionics, as described, for example, in WO 94/22800, published Oct. 13, 1994 by Olin Corporation).

Nonionic co-surfactants can optionally contain propylene oxide in an amount up to about 15% by weight. Other preferred nonionic co-surfactants can be prepared by the processes described in U.S. Pat. No. 4,223,163, issued Sep. 16, 1980, Builloty, incorporated herein by reference.

Low cloud point nonionic co-surfactants additionally comprise a polyoxyethylene, polyoxypropylene block polymeric compound. Block polyoxyethylene-polyoxypropylene polymeric compounds include those based on ethylene glycol, propylene glycol, glycerol, trimethylolpropane and ethylenediamine as initiator reactive hydrogen compound. Certain of the block polymer surfactant compounds designated PLURONIC®, REVERSED PLURONIC®, and TETRONIC® by the BASF-Wyandotte Corp., Wyandotte, Mich., are suitable in ADD compositions of the invention. Preferred examples include REVERSED PLURONIC® 25R2 and TETRONIC® 702, Such co-surfactants are typically useful herein as low cloud point nonionic surfactants.

As used herein, a "high cloud point nonionic co-surfactant" can be defined as a nonionic surfactant system ingredient having a cloud point of greater than 40□ C., preferably greater than about 50□ C., and more preferably greater than about 60□ C. Preferably the nonionic co-surfactant system can comprise an ethoxylated surfactant derived from the reaction of a monohydroxy alcohol or alkylphenol containing from about 8 to about 20 carbon atoms, with from about 6 to about 15 moles of ethylene oxide per mole of alcohol or alkyl phenol on an average basis. Such high cloud point nonionic co-surfactants include, for example, Tergitol 15S9 (supplied by Union Carbide), Rhodasurf TMD 8.5 (supplied by Rhone Poulenc), and Neodol 91-8 (supplied by Shell).

It can be also preferred for purposes of the present invention that the high cloud point nonionic co-surfactant further have a hydrophile-lipophile balance ("HLB"; see Kirk Othmer hereinbefore) value within the range of from about 9 to about 15, preferably 11 to 15. Such materials include, for example, Tergitol 15S9 (supplied by Union Carbide), Rhodasurf TMD 8.5 (supplied by Rhone Poulenc), and Neodol 91-8 (supplied by Shell).

Another preferred high cloud point nonionic co-surfactant can be derived from a straight or preferably branched chain or secondary fatty alcohol containing from about 6 to about 20 carbon atoms ($C_6$-$C_{20}$ alcohol), including secondary alcohols and branched chain primary alcohols. Preferably, high cloud point nonionic co-surfactants are branched or secondary alcohol ethoxylates, more preferably mixed C9/11 or C11/15 branched alcohol ethoxylates, condensed with an average of from about 6 to about 15 moles, preferably from about 6 to about 12 moles, and most preferably from about 6 to about 9 moles of ethylene oxide per mole of alcohol. Preferably the ethoxylated nonionic co-surfactant so derived has a narrow ethoxylate distribution relative to the average.

When the optional co-surfactants are a mixture of low cloud point nonionics and high cloud point nonionics it can be preferred that the mixture can be combined in a weight ratio preferably within the range of from about 10:1 to about 1:10.

The anionic co-surfactant can be selected from alkylethoxycarboxylates, alkylethoxysulfates, with the degree of ethoxylation greater than 3 (preferably 4 to 10; more preferably 6 to 8), and chain length in the range of C8 to C16, preferably 11-15. Additionally, branched alkylcarboxylates have been found to be useful in ADD compositions when the branch occurs in the middle and the average total chain length can be 10 to 18, preferably 12-16 with the side branch 2-4 carbons in length. An example can be 2-butyloctanoic acid. The anionic co-surfactant can be typically of a type having good solubility in the presence of calcium. Such anionic co-surfactants are further illustrated by alkyl(polyethoxy)sulfates (AES), alkyl (polyethoxy)carboxylates (AEC), and short chained $C_6$-$C_{10}$ alkyl sulfates and sulfonates. Straight chain fatty acids have been shown to be ineffective due to their sensitivity to calcium.

(c) Enzyme

"Detergent enzyme", as used herein, means any enzyme having a cleaning, stain removing or otherwise beneficial effect in an ADD composition. Preferred enzymes are hydrolases such as proteases, amylases and lipases. Highly preferred for automatic dishwashing are amylases and/or proteases, including both current commercially available types and improved types which, though more bleach compatible, have a remaining degree of bleach deactivation susceptibility.

Enzyme-containing compositions, especially liquid compositions, herein can comprise from about 0.001% to about 10%, preferably from about 0.005% to about 8%, most preferably from about 0.01% to about 6%, by weight of an enzyme stabilizing system. The enzyme stabilizing system can be any stabilizing system which can be compatible with the detersive enzyme. Such stabilizing systems can comprise calcium ion, boric acid, propylene glycol, short chain carboxylic acid, boronic acid, and mixtures thereof.

One embodiment of the present invention relates to a liquid, liquitab, and/or gel automatic dishwashing composition for treating tableware in an automatic dishwashing appliance comprising an electrochemical cell for improved tableware cleaning, sanitizing, and/or stain removal, the composition comprising: (a) at least about 0.1%, by weight of the composition, of a halogenated salt having the formula $(M)_x(X)_y$, wherein X can be Cl, Br, or I and wherein M can be a metal ion or cationic entity, and wherein x and y are chosen such that the salt can be charge balanced; (b) a component selected from the group consisting of a builder, suds suppressor, perfume, enzyme, bleach-scavenging agent, a metal-protecting agent, and mixtures thereof; and (c) an effective amount of an enzyme; and (d) an effective amount of a thickening agent; wherein the liquid, liquitab, and/or gel composition can be optionally free of bleach. Another embodiment of the present invention relates to an ADD composition, wherein the composition does not contain chlorine bleach, oxygen bleach, or mixtures thereof.

The ADD compositions herein optionally comprise one or more enzymes. If only one enzyme can be used, it can be preferably an amyolytic enzyme. Highly preferred for automatic dishwashing can be a mixture of proteolytic enzymes and amyloytic enzymes. More generally, the enzymes to be incorporated include proteases, amylases, lipases, cellulases, and peroxidases, as well as mixtures thereof. Other types of enzymes can also be included. They can be of any suitable origin, such as vegetable, animal, bacterial, fungal and yeast origin. However, their choice can be governed by several factors such as pH-activity and/or stability optima, thermostability, stability versus active detergents, builders, etc. In this respect bacterial or fungal enzymes are preferred, such as bacterial amylases and proteases, and fungal cellulases.

Enzymes are normally incorporated in the instant detergent compositions at levels sufficient to provide a "cleaning-effective amount". The term "cleaning-effective amount" refers to any amount capable of producing a cleaning, stain removal or soil removal effect on substrates such as fabrics, tableware and the like. Since enzymes are catalytic materials, such amounts can be very small. In practical terms for current commercial preparations, typical amounts are up to about 5 mg by weight, more typically about 0.01 mg to about 3 mg, of active enzyme per gram of the composition. Stated otherwise, the compositions herein will typically comprise from about 0.001% to about 6%, preferably 0.01%-1% by weight of a commercial enzyme preparation. Protease enzymes are usually present in such commercial preparations at levels sufficient to provide from 0.005 to 0.1 Anson units (AU) of activity per gram of composition. For automatic dishwashing purposes, it can be desirable to increase the active enzyme content of the commercial preparations, in order to minimize the total amount of non-catalytically active materials delivered and thereby improve spotting/filming results.

Suitable examples of proteases are the subtilisins which are obtained from particular strains of *B. subtilis* and *B. licheniformis*. Another suitable protease can be obtained from a strain of *Bacillus*, having maximum activity throughout the pH range of 8-12, developed and sold by Novo Industries A/S as ESPERASE®. The preparation of this enzyme and analogous enzymes can be described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

An especially preferred protease, referred to as "Protease D", as described in U.S. Pat. No. 5,679,630, Baeck, et al, and U.S. Pat. No. 5,677,272, Ghosh, et al, both incorporated herein by reference. Amylases suitable herein include, for example, α-amylases described in British Patent Specification No. 1,296,839 (Novo).

Engineering of enzymes (e.g., stability-enhanced amylase) for improved stability, e.g., oxidative stability can be known.

See, for example, J. Biological Chem., Vol. 260, No. 11, June 1985, pp 6518-6521. "Reference amylase" refers to a conventional amylase inside the scope of the amylase component of this invention. Further, stability-enhanced amylases, also within the invention, are typically compared to these "reference amylases".

The present invention, in certain preferred embodiments, can make use of amylases having improved stability in detergents, especially improved oxidative stability. A convenient absolute stability reference-point against which amylases used in these preferred embodiments of the instant invention represent a measurable improvement can be the stability of TERMAMYL® in commercial use in 1993 and available from Novo Nordisk A/S. This TERMAMYL® amylase can be a "reference amylase", and can be itself well-suited for use in the ADD compositions of the invention.

Even more preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9-10; thermal stability, e.g., at common wash temperatures such as about 60° C.; or alkaline stability, e.g., at a pH from about 8 to about 11, all measured versus the above-identified reference-amylase. Preferred amylases herein can demonstrate further improvement versus more challenging reference amylases, the latter reference amylases being illustrated by any of the precursor amylases of which preferred amylases within the invention are variants. Such precursor amylases can themselves be natural or be the product of genetic engineering. Stability can be measured using any of the art-disclosed technical tests. See references disclosed in WO 94/02597.

In general, stability-enhanced amylases respecting the preferred embodiments of the invention can be obtained from Novo Nordisk A/S, or from Genencor International. Preferred amylases herein have the commonality of being derived using site-directed mutagenesis from one or more of the *Baccillus* amylases, especialy the *Bacillus* alpha-amylases, regardless of whether one, two or multiple amylase strains are the immediate precursors.

Such amylases are non-limitingly illustrated by the following:

(i) An amylase according to the hereinbefore incorporated WO/94/02597, Novo Nordisk A/S, published Feb. 3, 1994, as further illustrated by a mutant in which substitution can be made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens*, *B. subtilis*, or *B. stearothermophilus*;

(ii) Stability-enhanced amylases as described by Genencor International in a paper entitled "Oxidatively Resistant alpha-Amylases" presented at the 207th American Chemical Society National Meeting, Mar. 13-17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8,15,197,256,304,366 and 438 leading to specific mutants, particularly important being M197L and M197T with the M197T variant being the most stable expressed variant. Stability was measured in CASCADE® and SUNLIGHT®;

(iii) Particularly preferred herein are amylase variants having additional modification in the immediate parent available from Novo Nordisk A/S. These amylases do not yet have a tradename but are those referred to by the supplier as QL37+ M197T.

Any other oxidative stability-enhanced amylase can be used, for example as derived by site-directed mutagenesis from known chimeric, hybrid or simple mutant parent forms of available amylases.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, and in the above incorporated U.S. Pat. No. 6,143,707, Trinh et al, issued Nov. 7, 2000. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

(d) Chelating Agents

The compositions herein can also optionally contain one or more transition-metal selective sequestrants, "chelants" or "chelating agents", e.g., iron and/or copper and/or manganese chelating agents. Chelating agents suitable for use herein can be selected from the group consisting of aminocarboxylates, phosphonates (especially the aminophosphonates), polyfunctionally-substituted aromatic chelating agents, and mixtures thereof. Without intending to be bound by theory, it can be believed that the benefit of these materials can be due in part to their exceptional ability to control iron, copper and manganese in washing solutions which are known to decompose hydrogen peroxide and/or bleach activators; other benefits include inorganic film prevention or scale inhibition. Commercial chelating agents for use herein include the DEQUEST® series, and chelants from Monsanto, DuPont, and Nalco, Inc.

Aminocarboxylates useful as optional chelating agents are further illustrated by ethylenediaminetetracetates, N-hydroxyethylethylenediaminetriacetates, nitrilo-triacetates, ethylenediamine tetraproprionates, triethylenetetraaminehexacetates, diethylenetriamine-pentaacetates, and ethanoldiglycines, alkali metal, ammonium, and substituted ammonium salts thereof. In general, chelant mixtures can be used for a combination of functions, such as multiple transition-metal control, long-term product stabilization, and/or control of precipitated transition metal oxides and/or hydroxides.

Polyfunctionally-substituted aromatic chelating agents are also useful in the compositions herein. See U.S. Pat. No. 3,812,044, issued can 21, 1974, to Connor et al. Preferred compounds of this type in acid form are dihydroxydisulfobenzenes such as 1,2-dihydroxy-3,5-disulfobenzene.

A highly preferred biodegradable chelator for use herein can be ethylenediamine disuccinate ("EDDS"), especially (but not limited to) the [S,S] isomer as described in U.S. Pat. No. 4,704,233, Nov. 3, 1987, to Hartman and Perkins. The trisodium salt can be preferred though other forms, such as magnesium salts, can also be useful.

Aminophosphonates are also suitable for use as chelating agents in the compositions of the invention when at least low levels of total phosphorus are acceptable in detergent compositions, and include the ethylenediaminetetrakis (methylenephosphonates) and the diethylenetriaminepentakis (methylene phosphonates). Preferably, these aminophosphonates do not contain alkyl or alkenyl groups with more than about 6 carbon atoms.

If utilized, chelating agents or transition-metal-selective sequestrants will preferably comprise from about 0.001% to about 10%, more preferably from about 0.05% to about 1% by weight of the compositions herein.

One embodiment of the present invention relates to an ADD composition comprising a chelant selected from the group consisting of EDTA, tetraacetyl ethylene diamine (TAED), EDDS, aminophosphonates, aminocarboxylates, carboxylatephosphonates, aluminosilicates, magnesioaluminosiliates, polyfunctionally-substituted aromatic chelating agents, and mixtures thereof.

(e) Dispersant Polymer

Preferred ADD compositions herein can additionally contain a dispersant polymer. When present, a dispersant polymer in the instant ADD compositions can be typically at levels in the range from 0 to about 25%, preferably from about 0.5% to about 20%, more preferably from about 1% to about 8%, by weight of the ADD composition. Dispersant polymers are useful for improved filming performance of the present ADD compositions, especially in higher pH embodiments, such as those in which wash pH exceeds about 9.5. Particularly preferred are polymers which inhibit the deposition of calcium carbonate or magnesium silicate on dishware.

Dispersant polymers suitable for use herein are further illustrated by the film-forming polymers described in U.S. Pat. No. 4,379,080 (Murphy), issued Apr. 5, 1983. Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably can be from about 1,000 to about 500,000, more preferably can be from about 1,000 to about 250,000, and most preferably, especially if the ADD can be for use in North American automatic dishwashing appliances, can be from about 1,000 to about 5,000.

Other suitable dispersant polymers include those disclosed in U.S. Pat. Nos. 3,308,067, 4,530,766, 3,723,322, 3,929,107, 3,803,285, 3,629,121, 4,141,841, and 5,084,535; EP Pat. No. 66,915.

Copolymers of acrylamide and acrylate having a molecular weight of from about 3,000 to about 100,000, preferably from about 4,000 to about 20,000, and an acrylamide content of less than about 50%, preferably less than about 20%, by weight of the dispersant polymer can also be used.

Particularly preferred dispersant polymers are low molecular weight modified polyacrylate copolymers. Suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and can be the fully neutralized form of the polymer comprising about 70% by weight acrylic acid and about 30% by weight methacrylic acid.

Other dispersant polymers useful herein include the polyethylene glycols and polypropylene glycols having a molecular weight of from about 950 to about 30,000 which can be obtained from the Dow Chemical Company of Midland, Mich.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate can be the most preferred polymer of this group. Yet another group of acceptable dispersants are the organic dispersant polymers, such as polyaspartate.

One embodiment of the present invention relates to an ADD composition comprising a dispersant polymer selected from the group consisting of poly (acrylic/allyl alcohol), poly (acrylic/maleic), poly (a-hydroxyacrylic acid), poly (tetramathylene-1,2-dicarbocylic acid), poly (4-methocy-tetramethylene-1,2-tetramethylene-1,2-dicarbocylic acid), polyacrylates, acrylic acid/maleic acid copolymers, polyalkyleneglycols, polyaminoacids, carboxyalkylcelluloses, alkylated or hydroxyalkylated celluloses, ether hydroxypolycarboxylates, polyvinylpyrrolidone, polyvinylpyridine-N-oxide, poly(vinylpyrrolidone)-co-poly(vinylimidazole), polydimethylsiloxanes, polydimethylsiloxanes, trisiloxanes with pendant polyethylene, polyethylene/polypropylene sidechains, water soluble salts, and combinations thereof.

(c) Thickeners

The physical stability of the liquid or gel product can be improved, and the thickness of the product can be altered, by the addition of a cross-linking thickener to the liquid or gel detergent product as a thixotropic thickener.

Thickeners for use herein include those selected from clay, polycarboxylates, such as Polygel®, gums, carboxymethyl cellulose, polyacrylates, and mixtures thereof. The preferred clay type herein has a double-layer structure. The clay can be naturally occurring, e.g., Bentonites, or artificially made, e.g., Laponite®. Laponite® can be supplied by Southern Clay Products, Inc. See *The Chemistry and Physics of Clays*, Grimshaw, $4^{th}$ ed., 1971, pages 138-155, Wiley-Interscience.

One embodiment of the present invention relates to an ADD composition comprising a nanoparticle and/or functional colloidal particle selected from the group consisting of: (a) inorganic metal oxides, natural clays, synthetic clays and mixtures thereof; (b) synthetic clays selected from the group consisting of kaolinite, montmorillinite/smectite, smectite, hectorite, synthetic flurohectorite, illite, variants and isomorphous substitutions of the synthetic clay groups and mixtures thereof; and (c) synthetic clays selected from the group consisting of layered hydrous silicate, layered hydrous aluminum silicate, fluorosilicate, mica-montmorillonite, hydrotalcite, lithium magnesium silicate, lithium magnesium fluorosilicate and mixtures thereof.

(d) Functionalized Surface Molecules

The functionalized surface molecule of the present invention can be present in the composition to provide hydrophilic or hydrophobic character to the composition, to anchor and/or enhance surface adsorption of the tableware, and/or to provide water-affinity to treated tableware.

One embodiment of the present invention relates to an ADD composition comprising a functionalized surface molecule or component and/or compound selected from the group consisting of monomeric materials, polymers, copolymers and mixtures thereof, wherein at least one segment and/or group of the monomeric material and/or polymer can comprise functionality selected from the group consisting of providing hydrophilic or hydrophobic character to the monomeric material and/or polymer, anchoring and/or enhancing adsorption on solid surfaces, providing water-affinity to the monomeric material and/or polymer, and combinations thereof.

(e) pH Adjusting Components

The above liquid or gel detergent product can be preferably low foaming, readily soluble in the washing medium and most effective at pH values best conducive to improved cleaning performance, such as in a range of desirably from about pH 6.5 to about pH 12.5, and preferably from about pH 7.0 to about pH 12.0, more preferably from about pH 8.0 to about pH 12.0. Preferably the pH can be less than about 10.0 for better enzyme stability, most preferably less than about 9.0. The pH adjusting components are desirably selected from sodium or potassium hydroxide, sodium or potassium carbonate or sesquicarbonate, sodium or potassium silicate, boric acid, sodium or potassium bicarbonate, sodium or potassium borate, and mixtures thereof. NaOH or KOH are the preferred ingredients for increasing the pH to within the above ranges. Other preferred pH adjusting ingredients are sodium carbonate, potassium carbonate, and mixtures thereof.

(f) Organic Solvent

One embodiment of the present invention relates to an ADD composition comprising an organic solvent selected from the group consisting of low molecular weight aliphatic or aromatic alcohols, low molecular weight alkylene glycols, low molecular weight alkylene glycol ethers, low molecular weight esters, low molecular weight alkylene amines, low molecular weight alkanolamines, and mixtures thereof.

(g) Bleach, Bleach, Bleach Catalyst and/or Bleach Activator

One embodiment of the present invention relates to an ADD composition comprising a bleach, bleach catalyst and/or bleach activator can be selected from the group consisting of benzoyl peroxide, ε-phthalimidoperoxyhexanoic acid, 6-nonylamino-6-oxoperoxycaproic acid, tetraacetyl ethylene diamine, benzoylcaprolactam, nonanoyloxybenzenesulphonate (NOBS), decanoyloxybenzenesulphonate, (6-octanamidocaproyl)oxybenzenesulfonate, (6-nonanamidocaproyl) oxybenzenesulfonate, (6-decanamidocaproyl) oxybenzenesulfonate, magnesium monoperoxyphthalate, quaternary substituted bleach activators, and mixtures thereof.

(h) Electrochemically-Activated Pro-Benefit Agent

Another embodiment of the present invention relates to an ADD composition comprising an electrochemically-activated pro-benefit agent selected from the group consisting of pro-perfume, pro-oxidant, pro-reductant, pro-surface active agent, pro-glass care agent, and mixtures thereof, wherein when the electrochemically-activated pro-benefit agent is exposed to at least one electrochemical cell it undergoes oxidation and/or reduction and can be thereby converted into an active agent which provides a treatment benefit to tableware upon contact with the tableware, and wherein the benefit can be selected from the group consisting of cleaning, aesthetic, disinfecting, stain-removal, dish-care, and combinations thereof.

(i) Moisture Content

Since ADD compositions herein can contain water-sensitive ingredients or ingredients which can co-react when brought together in an aqueous environment, it can be desirable to keep the free moisture content of the ADDs at a minimum, e.g., 7% or less, preferably 4% or less of the ADD; and to provide packaging which can be substantially impermeable to water and carbon dioxide. Coating measures have been described herein to illustrate a way to protect the ingredients from each other and from air and moisture. Plastic bottles, including refillable or recyclable types, as well as conventional barrier cartons or boxes are another helpful means of assuring maximum shelf-storage stability. As noted, when ingredients are not highly compatible, it can further be desirable to coat at least one such ingredient with a low-foaming nonionic surfactant for protection. There are numerous waxy materials which can readily be used to form suitable coated particles of any such otherwise incompatible components; however, the formulator prefers those materials which do not have a marked tendency to deposit or form films on dishes including those of plastic construction.

One embodiment of the present invention relates to an ADD composition, wherein the composition can be present in the form selected from the group consisting of liquid, gel, tablet, powder, water-soluble pouch, and mixtures thereof.

Method for Treating Soiled Tableware

The present invention also relates to a method of treating tableware in an automatic dishwashing appliance comprising an electrochemical cell and/or electrolytic device that results in improved tableware cleaning, sanitizing, and/or stain removal, the method comprising the steps of: (a) placing tableware in need of treatment in the appliance; (b) providing an automatic dishwashing composition comprising a component selected from the group consisting of halogenated salt, phosphate, silicate, suds suppressor, perfume, bleach-scavenging agent, metal-protecting agent, and mixtures thereof, during a wash and/or a rinse cycle in the appliance; (c) passing an aqueous electrolytic solution through the electrochemical cell to generate at least some electrolyzed water in the wash and/or rinse liquor of the appliance; and (d) contacting the tableware with the electrolyzed water.

This invention also encompasses a method of washing tableware in a domestic or commercial automatic dishwashing appliance, comprising treating the soiled tableware in an automatic dishwasher with an aqueous bath comprising the above ADD composition.

This invention also encompasses a method for cleaning, sanitizing and removing stains of soiled tableware comprising use of a separate composition in conjunction with electrolyzed water, such as at least one product selected from the group consisting of a solid electrolysis precursor compound of low water solubility, an electrolysis precursor compound containing a matrix of low water solubility, and mixtures thereof, for treatment, pre-treatment, or post-treatment of tableware in an automatic dishwashing appliance can be used in conjunction with the electrolysis process of the present invention.

The method of use can also incorporate the steps of providing and dispensing a bleach-scavenging agent to deactivate the halogenated mixed oxidants that were generated by the electrolysis process. The chlorine bleach-scavenging agent can be released subsequent to the period of electrolysis, or during one or more of the rinses to deactivate the above-mentioned halogenated mixed oxidants.

The electrolyzed water that exits the electrolytic device of this invention can effectively disinfect and/or sanitize the aqueous electrolytic solution comprising tap water, wash and/or rinse liquor solution, recirculated wash and/or rinse liquor, and mixtures thereof, making the aqueous electrolytic solution useful for treating tableware in automatic dishwashing appliances by providing cleaning, sanitization, and stain removal benefits in both commercial, as well as, in residential applications. The attached, integrated, recirculating electrolytic device of the automatic dishwashing appliance can be used for cleaning, sanitization, and stain removal tableware in all types of applications.

Though recirculation of the wash and/or rinse liquor provides for continuous production of newly electrolyzed halogenated mixed oxidants that will be available immediately during specific times of the wash and/or rinse cycles, it can be highly preferred to use the electrolyzed electrolytic solution immediately after the electrolysis, since the beneficial biocidal halogenated mixed oxidants have a short life span. Preferably, the aqueous electrolytic solution, when used for disinfection and/or sanitization or sterilization, can be used within about 15 minutes, preferably within about 5 minutes, more preferably within about 1 minute, and most preferably almost immediately, after electrolysis.

One embodiment of the present invention relates to a method of treating tableware in an automatic dishwashing appliance comprising an electrochemical cell and/or electrolytic device that results in improved tableware cleaning, sanitizing, and/or stain removal, the method comprising the steps of: (a) placing tableware in need of treatment in the appliance; (b) providing an automatic dishwashing composition comprising a component selected from the group consisting of halogenated salt, builder, suds suppressor, perfume, bleach-scavenging agent, metal-protecting agent, and mixtures thereof, during a wash and/or a rinse cycle in the appliance; (c) passing an aqueous electrolytic solution through the electrochemical cell and/or electrolytic device to generate at least some electrolyzed water in the wash and/or rinse liquor of the appliance; and (d) contacting the tableware with the electrolyzed water.

Another embodiment of the present invention relates to a method further can comprise the step of providing the composition for an additional and/or separate dispensing during the wash and/or rinse cycles in the appliance after the step of initially contacting the tableware with the electrolyzed water. After the step of initially contacting the tableware with the electrolyzed water, the method can also further comprise steps of providing an ADD composition comprising a component selected from the group consisting of bleach-scavenging agent, metal-protecting agent, and mixtures thereof, and subsequently contacting the tableware with a wash and/or rinse liquor comprising the composition. The method can further comprise repeating all and/or individual steps until the tableware needing treatment can be treated It can be preferred that when the composition comprising bleach-scavenging agent, metal-protecting agent, and mixtures thereof, can be provided, no further electrolyzed water comes into contact with the tableware.

Another embodiment of the present invention relates to a method, wherein the builder can be selected from the group consisting of phosphate, phosphate oligomers or polymers and salts thereof, silicate oligomers or polymers and salts thereof, aluminosilicates, magnesioaluminosiliates, citrate, and mixtures thereof. The composition can further comprise a chelant selected from the group consisting of EDTA, tetraacetyl ethylene diamine (TAED), EDDS, aminophosphonates, aminocarboxylates, carboxylatephosphonates, aluminosilicates, magnesioaluminosiliates, polyfunctionally-substituted aromatic chelating agents, and mixtures thereof.

Another embodiment of the present invention relates to a method, wherein the anti-corrosion agents and/or anti-tarnishing agents comprise a compound selected from the group consisting of sodium silicate, magnesium silicate, benzotriazole, fatty acid salts of aluminum, and mixtures thereof.

Another embodiment of the present invention relates to a method, wherein the composition further can comprise a dispersant polymer selected from the group consisting of poly (acrylic/allyl alcohol), poly (acrylic/maleic), poly (a-hydroxyacrylic acid), poly (tetramathylene-1,2-dicarbocylic acid), poly (4-methocy-tetramethylene-1,2-tetramethylene-1,2-dicarbocylic acid), polyacrylates, acrylic acid/maleic acid copolymers, polyalkyleneglycols, polyaminoacids, carboxyalkylcelluloses, alkylated or hydroxyalkylated celluloses, ether hydroxypolycarboxylates, polyvinylpyrrolidone, polyvinylpyridine-N-oxide, poly(vinylpyrrolidone)-co-poly(vinylimidazole), polydimethylsiloxanes, polydimethylsiloxanes, trisiloxanes with pendant polyethylene, polyethylene/polypropylene sidechains, water soluble salts, and combinations thereof.

Another embodiment of the present invention relates to a method, wherein the composition can comprise a surfactant can be selected from the group consisting of anionic surfactants, cationic surfactants, nonionic surfactants, amphoteric surfactants, ampholytic surfactants, zwitterionic surfactants, and mixtures thereof.

Another embodiment of the present invention relates to a method, wherein the composition can comprise a nanoparticle and/or functional colloidal particle selected from the group consisting of: (a) inorganic metal oxides, natural clays, synthetic clays and mixtures thereof; (b) synthetic clays selected from the group consisting of kaolinite, montmorillinite/smectite, smectite, hectorite, synthetic flurohectorite, illite, variants and isomorphous substitutions of the synthetic clay groups and mixtures thereof; and (c) synthetic clays selected from the group consisting of layered hydrous silicate, layered hydrous aluminum silicate, fluorosilicate, mica-montmorillonite, hydrotalcite, lithium magnesium silicate, lithium magnesium fluorosilicate and mixtures thereof.

Another embodiment of the present invention relates to a method, wherein the composition the functionalized surface molecule can comprise a component and/or compound selected from the group consisting of monomeric materials, polymers, copolymers and mixtures thereof, wherein at least one segment and/or group of the monomeric material and/or polymer can comprise functionality selected from the group consisting of providing hydrophilic or hydrophobic character to the monomeric material and/or polymer, anchoring and/or enhancing adsorption on solid surfaces, providing water-affinity to the monomeric material and/or polymer, and combinations thereof.

Another embodiment of the present invention relates to a method, wherein the composition(s) do not contain chlorine bleach, oxygen bleach, and mixtures thereof.

Another embodiment of the present invention relates to a method, wherein the composition can comprise NaCl, KCl, and mixtures thereof, at a level of greater than about 0.1%, preferably at a level greater than about 0.5% by weight of the composition, more preferably at a level of greater than about 1% by weight of the composition. And most preferably at a level of greater than about 2%, by weight of the composition.

Another embodiment of the present invention relates to a method, wherein the composition can comprise an organic solvent selected from the group consisting of low molecular weight aliphatic or aromatic alcohols, low molecular weight alkylene glycols, low molecular weight alkylene glycol ethers, low molecular weight esters, low molecular weight alkylene amines, low molecular weight alkanolamines, and mixtures thereof.

Another embodiment of the present invention relates to a method, wherein the composition can comprise a suds suppressor selected from the group consisting of low-foaming nonionic surfactants, low-foaming nonionic surfactants with a cloud point below about 30° C., alkoxylates or mixed alkoxylates of linear fatty alcohols, alkoxylates or mixed alkoxylates of alkylphenols, block co-polymers of ethylene and propylene glycol, $C_{9/11}EO_8$-cyclohexyl acetal alkyl capped nonionic, $C_{11}EO_7$-n-butyl acetal, $C_{9/11}EO_8$-2-ethylhexyl acetal, $C_{11}EO_8$-pyranyl, alcohol alkoxylate, and mixtures thereof.

Another embodiment of the present invention relates to a method, wherein the composition can comprise a bleach, bleach catalyst and/or bleach activator can be selected from the group consisting of benzoyl peroxide, ε-phthalimidoperoxyhexanoic acid, 6-nonylamino-6-oxoperoxycaproic acid, tetraacetyl ethylene diamine, benzoylcaprolactam, nonanoyloxybenzenesulphonate (NOBS), decanoyloxybenzenesulphonate, (6-octanamidocaproyl)oxybenzenesulfonate, (6-nonanamidocaproyl)oxybenzenesulfonate, (6-decanamidocaproyl)oxybenzenesulfonate, magnesium monoperoxyphthalate, quaternary substituted bleach activators, and mixtures thereof.

Another embodiment of the present invention relates to a method, wherein the composition can comprise a bleach-scavenging agent selected from the group consisting of perborate, percarbonate, ascorbic acid or derivatives thereof, carbamate, ammonium, sulfite, bisulfite, aluminum tristearate, sodium silicate, benzotriazole, amines, amino acids, and mixtures thereof.

Another embodiment of the present invention relates to a method, wherein the composition can comprise an electrochemically-activated pro-benefit agent can comprise a compound selected from the group consisting of pro-perfume, pro-oxidant, pro-reductant, pro-surface active agent, pro-glass care agent, and mixtures thereof, wherein when the electrochemically-activated pro-benefit agent is exposed to at least one electrochemical cell it undergoes oxidation and/or reduction and can be thereby converted into an active agent which provides a treatment benefit to tableware upon contact with the tableware, and wherein the benefit can be selected from the group consisting of cleaning, aesthetic, disinfecting, stain-removal, dish-care, and combinations thereof.

Another embodiment of the present invention relates to a method, wherein the composition can comprise an electrode maintenance and/or descaling agents can be selected from the group consisting of citric acid, acetic acid, and mixtures thereof.

Another embodiment of the present invention relates to a method, wherein the composition can comprise an electrolytic device comprising at least one of the features selected from the group consisting of (a) a non-partitioned electrochemical cell; (b) at least one disposable and/or replaceable electrochemical cell component; (c) a recirculating system allowing for wash and/or rinse liquor to continuously circulate and/or recirculate through the electrolytic device, into the bulk wash or rinse liquor contained in the appliance, and back through the device; (d) an electrochemical cell comprising a cathode of stainless steel, an anode of titanium coated or layered with at least one of the materials selected from the group consisting of platinum, ruthenium, iridium, and oxides, alloys, and mixtures thereof, (e) a gap between the at least one pair of electrodes having a gap spacing between about 0.1 mm to about 0.5 mm, (f) an operating voltage of the electrolytic device and/or electrochemical cell between about 1.5 and about 220 volts; and combination thereof.

Another embodiment of the present invention relates to a method, wherein the composition can be used in the wash and/or rinse cycle of the appliance at temperatures from about 120 degrees F. and below.

Article of Manufacture

The present invention relates to an article of manufacture for an automatic dishwashing appliance comprising: (a) a package; (b) a replacement product comprising a component selected from electrolytic solution comprising halogen ions, halogenated salts having the formula $(M)_x(XO_2)_y$, and/or $(M)_x(X)_y$, wherein X can be Cl, Br, or I and wherein M can be a metal ion or cationic entity and wherein x and y are chosen such that the salt can be charge balanced, electrolysis precursor compound, a halogenated salt with low water solubility, a halogenated salt contained within a medium for controlled release, and mixtures thereof; (c) optionally, a replacement a porous basket comprising the product for dispensing; and (c) information in association with the package comprising instructions to insert the replacement components and/or the a porous basket in the appliance and/or the electrolytic device.

The present invention also relates to an article of manufacture, wherein the replacement product can be in the form such that once placed inside a dishwashing appliance it provides a controlled release of the electrolysis precursor compound into the wash and/or rinse liquors during operation of the automatic dishwasher over a: period of several weeks or months of regular household and/or commercial use.

Commercial Automatic Dishwashing Appliance

One embodiment of the present invention comprises ADD composition and/or method of using said composition in a commercial dishwasher appliance selected from the group consisting of conveyor-low-temperature type, cabinet-low-temperature type, and combinations thereof.

Composition of Matter

The present invention relates to an ADD composition of matter consisting essentially of the in the wash and/or rinse liquor of an automatic dishwashing appliance comprising an electrochemical cell and/or electrolytic device for improved tableware cleaning, sanitizing, and/or stain removal, the composition of matter comprising: (a) at least some electrolyzed water comprising halogenated mixed oxidants; (b) an ADD composition comprising a compound selected from the group consisting of a halogenated salts, halogenated salt with low water solubility, builder, suds suppressor, perfume, enzyme, bleach-scavenging agent, a metal-protecting agent, and mixtures thereof; (c) optionally, an ADD composition comprising a compound selected from the group consisting of an electrolytic composition comprising halogen ions, an electrolytic composition comprising halogenated salts having the formula $(M)_x(XO_2)_y$, and/or $(M)_x(X)_y$, wherein X can be Cl, Br, or I and wherein M can be a metal ion or cationic entity and wherein x and y are chosen such that the salt can be charge balanced, an electrolysis precursor compound, a halogenated salt with low water solubility, an electrolysis precursor compound contained within a medium for controlled release, and mixtures thereof; and (d) optionally, adjunct ingredients.

Another embodiment of the present invention relates to a composition of matter, wherein the operating temperature during the wash and/or rinse cycle(s) of said appliance is less than about 120° F. Thus, the composition of matter comprises a water temperature less than about 120° F.

EXAMPLES

Examples of formulations according to the present invention are as follows. All ingredients are expressed as weight % of the total formula composition.

|               | A       | B       | C       | D       | E       | F       | G       | H       |
|---------------|---------|---------|---------|---------|---------|---------|---------|---------|
| Builder[1]    | 25      | 25      | 30      | 30      | 30      | 30      | 20      | 20      |
| Na2CO3        | 25      | 25      | 10      | 10      | —       | —       | —       | —       |
| Silicate      | 10      | 10      | 8       | 8       | 10      | 12      | —       | —       |
| Enzymes[2]    | 1.0     | 2.0     | 2.0     | 2.0     | 1.0     | 2.0     | 3.0     | 4.0     |
| NaOH          | —       | —       | —       | —       | 1.0     | —       | 1.0     | 1.0     |
| Dispersant Polymer[3] | — | 0.5   | 1.0     | 1.0     | 0.5     | —       | 0.5     | 0.5     |
| Suds suppressor[4] | 1.0 | 1.0   | 1.5     | 1.5     | 1.0     | 1.5     | 2.0     | 2.0     |
| Halogenated salt[5] | 0.5 | 1.0  | 5.0     | 7.0     | 0.5     | 1.0     | 5.0     | 5.0     |
| Thickener[6]  | —       | —       | —       | —       | 0.5     | 0.5     | 0.7     | 0.7     |
| HEDP[7]       | —       | 0.5     | —       | —       | —       | 0.5     | —       | —       |
| Filler and adjuncts[8] | balance | balance | balance | Balance | balance | balance | balance | balance |

[1]Selected from Sodium tripolyphosphate, trisodium citrate.
[2]Selected from protease, amylase, and mixtures thereof.
[3]selected from polyacrylate, polyacrylate/polymethyacrylate, or polyacrylate/polymaleate co-polymers
[4]selected from Triton DF-18 (ex Dow ®), LF404 (ex BASF ®), SLF18 (ex Olin ®), and mixtures thereof.
[5]Having the formula $(M)_x(XO_2)_y$, wherein X can be F, Cl, Br, or I and wherein M can be a metal ion or cationic entity, and wherein x and y are chosen such that the salt can be charge balanced
[6]selected from Polygel DKP (ex 3V Co. ®), or Rheolate-5000 (ex Rheox ®)
[7]ethane 1-hydroxy-1,1-diphosphonic acid
[8]water, perfume, sodium sulfate, metal protection agents, and misc. etc.

Further examples of formulations according to the present invention are as follows. All ingredients are expressed as weight % of the total formula composition.

|                       | I       | J       | K       | L       |
|-----------------------|---------|---------|---------|---------|
| builder[1]            | 5       | 10      | 5       | —       |
| solvent[2]            | 10      | 10      | 10      | 10      |
| nonionic surfactant[3]| 15      | 15      | 20      | 10      |
| Polymer[4]            | —       | —       | 0.5     | —       |
| HEDP[5]               | —       | 1.0     | —       | —       |
| NaOH                  | —       | —       | —       | 0.2     |
| hydrotrope[6]         | 5       | 10      | —       | —       |
| Halogenated salt[7]   | 1.0     | 2.0     | 10      | 5.0     |
| Filler and adjuncts[8]| Balance | balance | balance | Balance |

[1]selected from citric acid, phosphoric acid, and mixtures thereof
[2]selected from ethanol, propylene glycol, dipropylene glycol
[3]selected from Triton DF-16 (ex Dow ®), Triton X-45 (ex Dow ®)
[4]selected from polyacrylate, polyacrylate/polymethyacrylate, or polyacrylate/polymaleate co-polymers
[5]ethane 1-hydroxy-1,1-diphosphonic acid
[6]selected from sodium cumenesulfonate, sodium xylenesulfonate
[7]Having the formula $(M)_x(XO_2)_y$, wherein X can be F, Cl, Br, or I and wherein M can be a metal ion or cationic entity, and wherein x and y are chosen such that the salt can be charge balanced
[8]water, perfume, sodium sulfate, metal protection agents, and misc. etc.

What is claimed is:

1. A method for cleaning, sanitizing, and/or removing stains from tableware comprising the steps of:
    A) forming an aqueous solution from a solid controlled release automatic dishwashing composition comprising:
        (a) at least about 0.1%, by weight of the composition, of a halogenated salt which is calcium chloride or magnesium chloride;
        (b) a component selected from the group consisting of a builder, suds suppressor, perfume, enzyme, bleach-scavenging agent, a metal-protecting agent, and mixtures thereof;
        (c) a dissolution control material; and
        (d) at least one adjunct ingredient; wherein said automatic dishwashing composition is free of bleach, and is in the form of a solid controlled release pill or tablet housed in a porous basket;
    B) allowing said aqueous solution to pass into an electrochemical cell and/or electrolytic device during the wash and/or rinse cycle, thereby forming an electrolytic solution comprising halogenated mixed oxidants; and
    C) contacting tableware with said electrolytic solution.

2. A method according to claim 1, wherein said halogenated salt is present at a level of greater than about 0.1% by weight of the composition.

3. A method according to claim 2, wherein said salt is present at a level of greater than about 0.5% by weight of the composition.

4. A method according to claim 2, wherein said salt is present at a level of greater than about 1.0% by weight of the composition.

5. A method according to claim 1, wherein said solid controlled automatic dishwashing composition provides a controlled release of steady levels of said halogenated salt into the wash and/or rinse liquors during operation of an automatic dishwasher over a period of from 1 day to 365 days of regular household and/or commercial use.

6. A method according to claim 5, wherein said porous basket comprises a material selected from the group consisting of glass, plastic, ceramic, metal, and combinations thereof.

7. A method according to claim 1, wherein said bleach-scavenging agent comprises a compound selected from the group consisting of ascorbic acid or derivatives thereof, carbamate, ammonium, sulfite, bisulfite, aluminum tristearate, sodium silicate, benzotriazole, amines, amino acids, and mixtures thereof.

8. A method according to claim 1 wherein said adjunct ingredient is selected from the group consisting of nanoparticles, functionalized surface molecules, polymers, surfactants, co-surfactants, metal ions, proteins, dyes, acids, bases, organic solvents, enzymes, enzyme stabilizing systems, chelants, optical brighteners, soil release agents, wetting agents, dispersants, blooming perfumes, colorants, filler salts, hydrotropes, preservatives, anti-oxidants, germicides, fungicides, color speckles, silvercare, anti-tarnishing agents, alkalinity sources, solubilizing agents, carriers, electrode maintenance and/or descaling agents, processing aids, pigments, and pH control agents, and mixtures thereof.

9. A method according to claim 2 wherein said builder is selected from the group consisting of phosphate, phosphate oligomers or polymers and salts thereof, silicate oligomers or polymers and salts thereof, aluminosilicates, magnesioaluminosiliates, citrate, and mixtures thereof.

10. A method according to claim 9, further comprising a chelant selected from the group consisting of EDTA, tetraacetyl ethylene diamine (TAED), EDDS, aminophosphonates, aminocarboxylates, carboxylatephosphonates, aluminosilicates, magnesioaluminosiliates, polyfunctionally-substituted aromatic chelating agents, and mixtures thereof.

11. A method according to claim 1, wherein said perfume is from about 0.01% to about 5%, by weight, a blooming perfume composition, wherein said blooming perfume composition comprises from about 50% to about 99% of blooming perfume ingredients having a boiling point of less than about 260° C. and a ClogP of at least about 3, and wherein said blooming perfume composition comprising at least about 5 different blooming perfume ingredients, and from about 0.5% to about 10% of base masking perfume ingredients having a boiling point of more than about 260° C. and a ClogP of at least about 3.

* * * * *